US008452063B2

(12) United States Patent
Wojton et al.

(10) Patent No.: US 8,452,063 B2
(45) Date of Patent: *May 28, 2013

(54) SHOWING SKIN LESION INFORMATION

(75) Inventors: Maciej Wojton, Roslyn Heights, NY (US); Mrinalini Roy, Thornwood, NY (US); Joanna S. Adrian, Brooklyn, NY (US)

(73) Assignee: MELA Sciences, Inc., Irvington, NY (US)

( * ) Notice: Subject to any disclaimer, the term of this patent is extended or adjusted under 35 U.S.C. 154(b) by 210 days.

This patent is subject to a terminal disclaimer.

(21) Appl. No.: 13/100,153

(22) Filed: May 3, 2011

(65) Prior Publication Data
US 2011/0210984 A1 Sep. 1, 2011

Related U.S. Application Data

(63) Continuation-in-part of application No. 12/916,656, filed on Nov. 1, 2010.

(60) Provisional application No. 61/280,386, filed on Nov. 3, 2009.

(51) Int. Cl.
G06K 9/00 (2006.01)

(52) U.S. Cl.
USPC .............................. 382/128; 705/3; 600/306

(58) Field of Classification Search
None
See application file for complete search history.

(56) References Cited

U.S. PATENT DOCUMENTS

| 4,817,044 | A | 3/1989 | Ogren |
| 6,081,612 | A | 6/2000 | Gutkowicz-Krusin et al. |
| 6,208,749 | B1 | 3/2001 | Gutkowicz-Krusin et al. |
| 6,307,957 | B1 | 10/2001 | Gutkowicz-Krusin et al. |
| 6,319,201 | B1 | 11/2001 | Wilk |
| 6,571,003 | B1 | 5/2003 | Hillebrand et al. |
| 6,626,558 | B2 | 9/2003 | Momot et al. |
| 6,726,101 | B1 | 4/2004 | McIntyre et al. |
| 6,993,167 | B1 | 1/2006 | Skladnev et al. |
| 7,041,941 | B2 | 5/2006 | Faries, Jr. et al. |
| 7,096,282 | B1 | 8/2006 | Wille |
| 7,102,672 | B1 | 9/2006 | Jacobs |
| 7,127,094 | B1 | 10/2006 | Elbaum et al. |
| 7,215,819 | B2 * | 5/2007 | Onno et al. .................... 382/240 |

(Continued)

FOREIGN PATENT DOCUMENTS

| EP | 1 505 765 | 2/2005 |
| EP | 1 658 817 | 5/2006 |

(Continued)

OTHER PUBLICATIONS

International Preliminary Report on Patentability for App. Ser. No. PCT/US2010/055273, dated May 8, 2012, 7 pages.

(Continued)

*Primary Examiner* — Bhavesh Mehta
*Assistant Examiner* — Siamak Harandi
(74) *Attorney, Agent, or Firm* — Fish & Richardson P.C.

(57) ABSTRACT

Among other things, on a two-dimensional electronic display are shown simultaneously: (a) at least a partial body view of a surface of the human model on which a location of a skin lesion on a corresponding real human has been indicated, and (b) an image of the lesion area that corresponds to the partial body view of the human model.

19 Claims, 60 Drawing Sheets
(56 of 60 Drawing Sheet(s) Filed in Color)

U.S. PATENT DOCUMENTS

| | | | |
|---|---|---|---|
| 7,233,693 | B2 | 6/2007 | Momma |
| 7,324,668 | B2 | 1/2008 | Rubinstenn et al. |
| 7,376,346 | B2 | 5/2008 | Merola et al. |
| 7,761,332 | B2 | 7/2010 | Capurso et al. |
| 7,920,714 | B2 * | 4/2011 | O'Neil ........................... 382/100 |
| 2001/0051787 | A1 | 12/2001 | Haller et al. |
| 2002/0010679 | A1 | 1/2002 | Felsher |
| 2002/0016720 | A1 | 2/2002 | Poropatich et al. |
| 2002/0021828 | A1 | 2/2002 | Papier et al. |
| 2002/0049432 | A1 | 4/2002 | Mukai |
| 2002/0059081 | A1 | 5/2002 | Yasuda et al. |
| 2003/0130567 | A1 | 7/2003 | Mault et al. |
| 2004/0068255 | A1 | 4/2004 | Short et al. |
| 2004/0255081 | A1 | 12/2004 | Arnouse |
| 2005/0049467 | A1 | 3/2005 | Stamatas et al. |
| 2006/0092315 | A1 | 5/2006 | Payonk et al. |
| 2006/0095297 | A1 | 5/2006 | Virik |
| 2007/0006322 | A1 | 1/2007 | Karimzadeh et al. |
| 2007/0043594 | A1 | 2/2007 | Lavergne |
| 2007/0078678 | A1 | 4/2007 | DiSilvestro et al. |
| 2007/0109527 | A1 | 5/2007 | Wenstrand |
| 2007/0127793 | A1 | 6/2007 | Beckett et al. |
| 2008/0214907 | A1 | 9/2008 | Gutkowicz-Krusin et al. |
| 2008/0312952 | A1 | 12/2008 | Gulfo et al. |
| 2009/0060304 | A1 | 3/2009 | Gulfo et al. |
| 2009/0080726 | A1 | 3/2009 | Cotton et al. |
| 2011/0103660 | A1 | 5/2011 | Butler et al. |

FOREIGN PATENT DOCUMENTS

| | | |
|---|---|---|
| JP | 11-070120 | 3/1999 |
| JP | 2001-046398 | 2/2001 |
| JP | 2002-011106 | 1/2002 |
| JP | 2009-506835 | 2/2009 |
| WO | WO 88/09973 | 12/1988 |
| WO | WO 03/001329 | 1/2003 |
| WO | WO 03/060650 | 7/2003 |
| WO | WO 2005/109297 | 11/2005 |
| WO | WO 2006/060286 | 6/2006 |
| WO | WO 2006/122741 | 11/2006 |
| WO | WO 2007/022017 | 2/2007 |
| WO | WO 2011/056851 | 5/2011 |
| WO | WO 2012/151128 | 11/2012 |

OTHER PUBLICATIONS

International Search Report and Written Opinion for App. Ser. No. PCT/US2012/035528, dated Nov. 28, 2012, 9 pages.

Office Action for Japanese App. Ser. No. 2010-512337, dated Dec. 18, 2012, 7 pages.

"HIPAA Compliance and Smart Cards: Solutions to Privacy and Security Requirements", Smart Card Alliance, Sep. 2003, pp. 1-46.

http://www.miaccard.com/miac_ps.html, Jun. 8, 2007, 1 page.

http://www.doctorsmile.cz/img/erbdiod.pdf, pp. 1-12. Jun. 12, 2007.

www.lambdascientifica.com/pagina.asp&lingua=&gruppo=9&categoria=39&id=134, KLS Smart Card, Jun. 12, 2007, 2 pages.

http://www.amo-inc.com, about AMO, Jun. 12, 2007, pp. 1-3.

Advanced Medical Optics, Inc., http://sec.edgar-online.com/2006/05/10/0001104659-06-033180/Section_8.asp, Mar. 31, 2006, pp. 1-17.

International Search Report for PCT/US08/66508 dated Sep. 25, 2008 (17 pages).

2006 Annual Form 10-K Report (Electro Optical Sciences) [online] Mar. 15, 2007 [retrieved on Oct. 9, 2008]. Retrieved from the Internet: URL:http://ccbn.10kwizard.com/xml/download.php?repo=tenk&ipage=4745835&format=PDF, p. 1, para 2-3; p. 8, para 5.

Electro-Optical Sciences, Inc., Needham & Co. 7$^{th}$ Annual Bio/MedTech Conference, Presentation re MELAFIND (Jun. 11, 2008, 35 pages).

Electro-Optical Sciences, Inc. 2008 Annual Report (Apr. 15, 2009, 88 pages).

Electro-Optical Sciences, Inc. 2007 Annual Report (Apr. 15, 2008, 96 pages).

Van Dusen, A., "Invasive biopsies may soon be a thing of the past if these detection methods prove effective," Forbes (Aug. 22, 2008, 3 pages).

Thumbnail image titled "eos-moneyshot.jpg" [retrieved on Jul. 27, 2009]. Retrieved from the Internet: http://images.google.com, and source code indicating that the thumbnail image was originally available at http://www.daniellicalzi.com in Jun. 2009 (2 pages).

Howard Teacher's Pet—Revolutionary Classroom Management [retrieved on Jul. 30, 2009]. Retrieved from the Internet: http://www.howardcomputers.com/petcart/ (6 pages).

FreelanceDesigners.org, Daniel LiCalzi, Live Beta [retrieved from the Internet on Jun. 26, 2009] (3 pages).

International Search Report for App. Ser. No. PCT/US2008/066636, dated Oct. 16, 2008, 16 pages.

International Preliminary Report on Patentability for App. Ser. No. PCT/US2008/066636, dated Dec. 17, 2009, 14 pages.

Supplementary European Search Report for App. Ser. No. EP 08 770 774, dated Aug. 23, 2010, 2 pages.

European Office Action for App. Ser. No. EP 08 770 774, dated Sep. 14, 2010, 11 pages.

Public Law 104-191 [H.R. 3103] Aug. 21, 1996, Health Insurance Portability and Accountability Act of 1966, 104 P.L. 191; 110 Stat. 1936; 1996 Enacted H.R. 3103; 104 Enacted H.R. 3103.

International Search Report and Written Opinion for App. Ser. No. PCT/US2010/055273, dated Jun. 23, 2011, 12 pages.

Office Action for Australian App. Ser. No. 2008266173, dated Feb. 28, 2013, 4 pages.

U.S. Appl. No. 11/761,816, filed Jun. 12, 2007.

U.S. Appl. No. 12/916,656, filed Nov. 1, 2010.

* cited by examiner 4.0

FIG. 50      5002

SHOWING SKIN LESION INFORMATION

RELATED APPLICATION

This application is a continuation-in-part of U.S. application Ser. No. 12/916,656, filed Nov. 1, 2010, which claims priority to U.S. provisional application Ser. 61/280,386, filed on Nov. 3, 2009, the entire contents of which are incorporated herein by reference.

BACKGROUND

This description relates to showing skin lesion information.

Skin lesion information, including scanned images of skin lesions and related data, can be stored on and displayed by computer to a dermatologist or other user to aid in diagnosis and treatment.

SUMMARY

In general, in an aspect, on a two-dimensional electronic display are shown simultaneously: (a) at least a partial body view of a surface of the human model on which a location of a skin lesion on a corresponding real human has been indicated, and (b) an image of the lesion area that corresponds to the partial body view of the human model.

Implementations may include one or more of the following features. Simultaneously with the partial body view and the image of the lesion, a thumbnail of the partial body view is shown. The partial body view bears an indication of the location of the skin lesion. The image comprises a reconstructed dermoscopic image. The image comprises a traditional dermoscopic image. A user can choose whether to display the image of the lesion or a model of the lesion.

In general, in an aspect, on a two-dimensional electronic display are shown an image of a lesion location and indications of skin lesions on the skin of a real human corresponding to the shown image. Legends are shown, for the respective skin lesions, each indicating a status of a corresponding skin lesion and a status of a scanned image of the skin lesion. The image comprises a reconstructed dermoscopic image. The image comprises a traditional dermoscopic image. The status of the scanned image comprises progress in completion of an analysis of the image. The legend comprises a color. The legend comprises an icon. The legend comprises a progress bar.

In general, in an aspect, on a two-dimensional electronic display are simultaneously shown: a list of rows where each row is an image representing the lesion location and the next diagnostic or treatment step in a column wise list format.

Implementations may include one or more of the following features. The image comprises a reconstructed dermoscopic image. The image comprises a traditional dermoscopic image. The next diagnostic or treatment step comprises biopsy. The next diagnostic or treatment step comprises observation. The next diagnostic or treatment step is indicated by a color.

These and other aspects and features, and combinations of them, can be expressed as methods, apparatus, program products, methods of doing business, systems, components, means for performing functions, and in other ways.

These and other aspects and features will become apparent from the following description and the claims.

DESCRIPTION

The patent or application file contains at least one drawing executed in color. Copies of this patent or patent application publication with colored drawing(s) will be provided by the patent office upon request and payment of the necessary fee.

Figure 1:
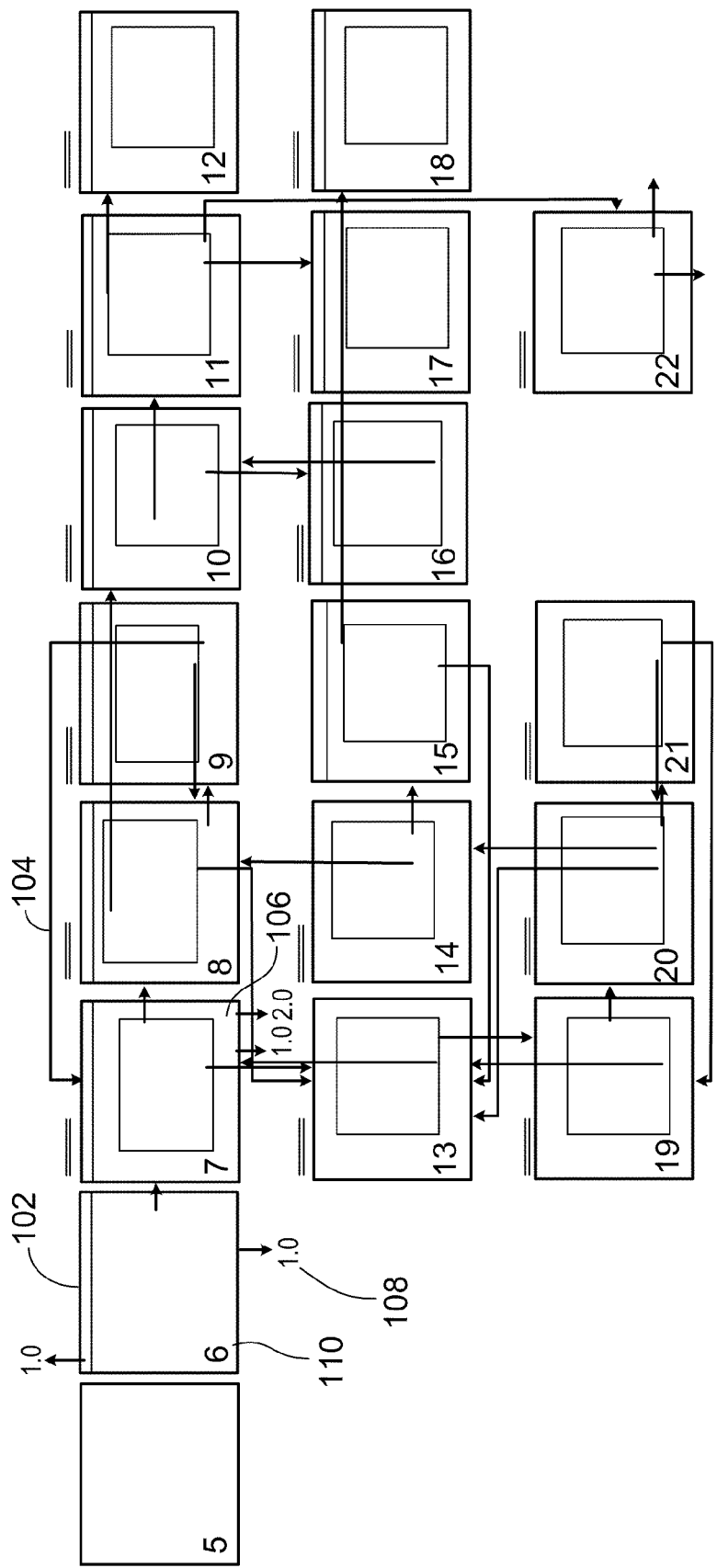
FIGS. 1 through 4 are flow diagrams.

By providing novel features in a user interface of a computer-implemented skin lesion information system, a dermatologist or other physician or other medical worker, researcher, or patient (or any other user) can (among other things) acquire, enter, store, review, analyze, annotate, process, manage, and use for diagnosis or treatment (among other things), skin lesion information (including scans of skin lesions, data about the scans, and any other kind of information about skin lesions), effectively, inexpensively, accurately, comfortably, quickly, and safely.

The features discussed here can be used alone or in combination with other user interfaces in a wide variety of skin lesion systems. The skin lesion systems can include general purpose and special purpose computers, machines, devices, equipment, and systems of any kind, including systems that have scanning devices, storage, memory, and display devices, for example. The implementations can use handheld devices, workstations, networks, and any other systems that process or store information or communicate it locally or remotely. When a computer is used in an implementation, the computer can have typical or special memory, storage, displays, keyboards, mice, communications capabilities, and other features. And a wide variety of operating systems, and application software can be used.

In some examples, the features of the user interface can be implemented on a mobile cart of the kind described in U.S. patent application Ser. Nos. 29/341,111, 29/341,114, and 12/512,775, all three filed on Jul. 30, 2009 Skin lesion information may be stored on and retrieved from memory devices of any kind including the memory cards or usage cards described in U.S. patent application Ser. No. 12/512,895, filed Jul. 30, 2009. Usages of the systems associated with usage cards can be monitored and controlled as described, for example, in U.S. patent application Ser. No. 11/761,816, filed Jun. 12, 2007. Additional information concerning user interfaces for skin lesion systems is found in U.S. patent application Ser. No. 11/681,345, filed Mar. 2, 2007. Additional information about identifying a location of a lesion on a human body is found in U.S. patent application Ser. No. 12/204,247, filed Sep. 4, 2008. All of the applications and patents identified here and elsewhere in this application are incorporated here by reference.

In some implementations, the lesion scanner used with the user interface can be a MelaFind probe developed by Electro-Optical Sciences, Inc., a multi-spectral scanner. Some information about the implementation of the MelaFind system can be found in United States patents and patent applications assigned to Electro-Optical Sciences, Inc., and incorporated here by reference, including U.S. Pat. Nos. 6,081,612; 6,208, 749; and 6,626,558.

FIGS. 1 through 4 respectively relate to flows experienced by users of a user interface in the contexts of administration, use of the system, use of a "phantom target" for testing functionality of a skin imaging device ("probe"), and practice scanning of a skin lesion. Each of the four figures presents the flow by showing blocks 102 corresponding to user interface screens. In each of the blocks, most of the detail of the user interface is not shown on FIGS. 1 through 4.

In general, but with some exceptions, the flow in each figure proceeds from left to right. Flow lines 104 in the figures connect user controls 106, such as buttons, in some of the screens, to other screens that appear when the user invokes the controls. In some cases, a flow line indicates a connection by pointing to a box 108 which contains a reference to the screen to which control is shifted. In each of the four figures, each of the thumbnails bears an identifying number to facilitate references to one another.

Figure 3:
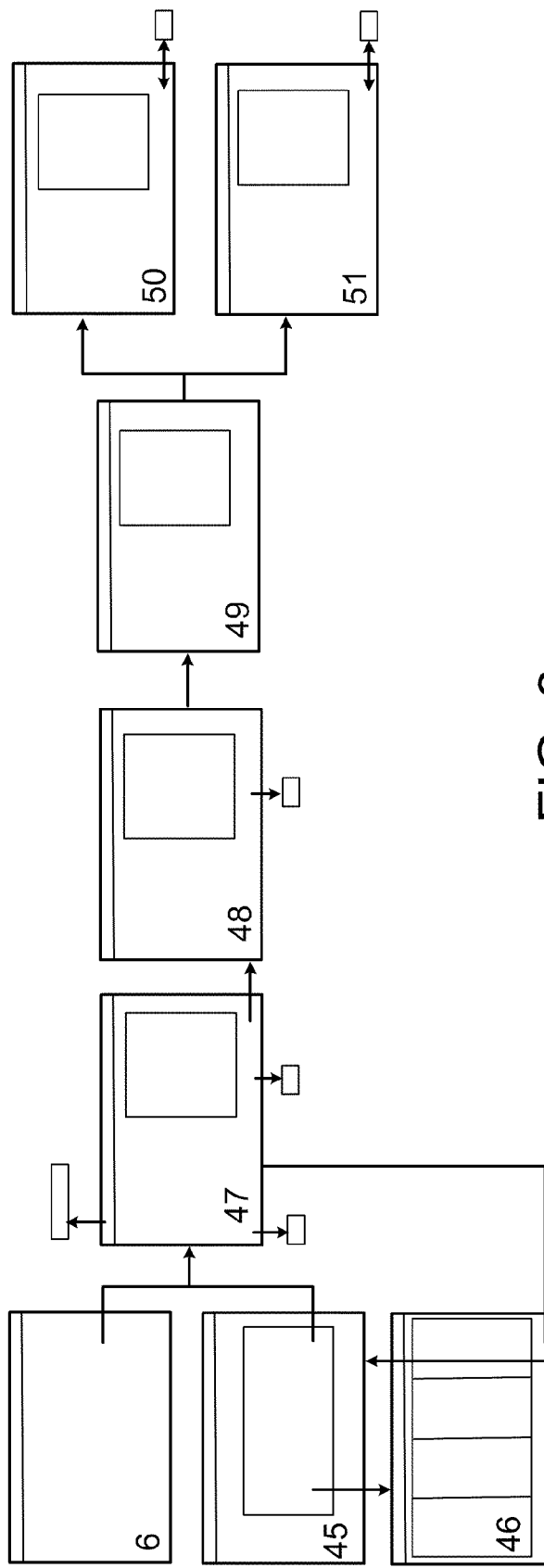
Figure 4:
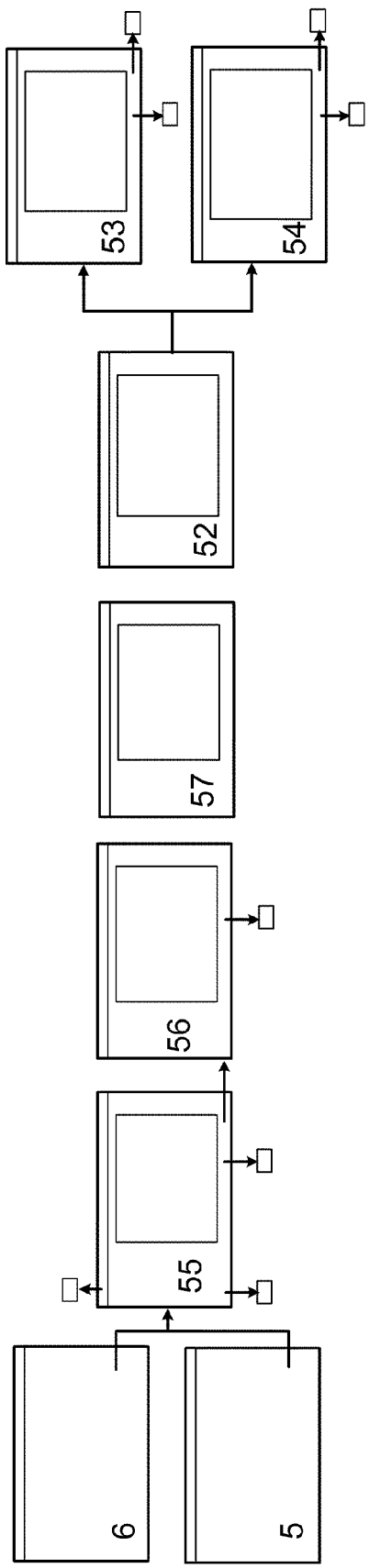
Figure 5:
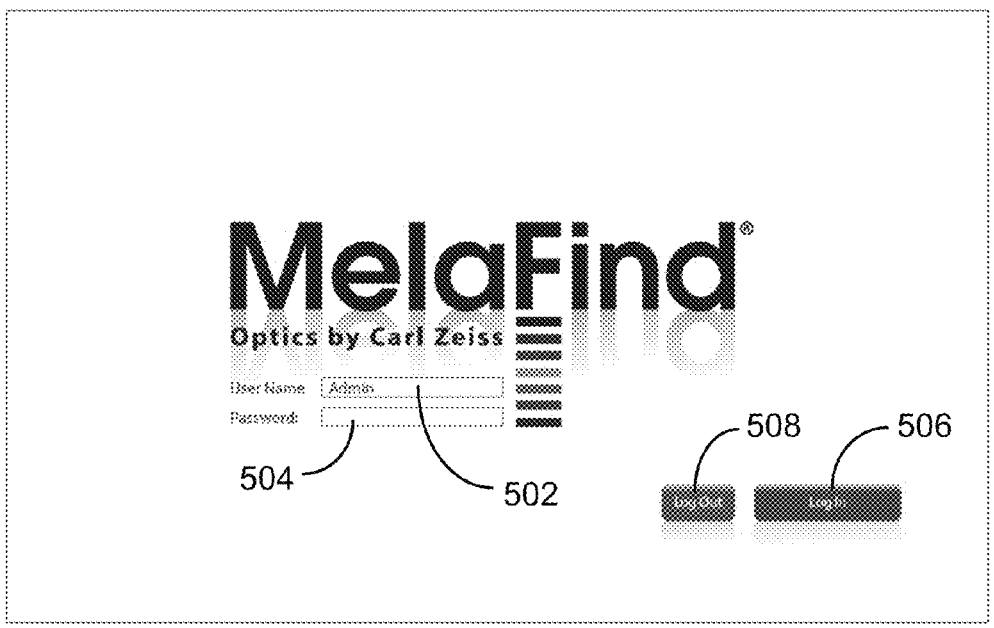
FIGS. 5 through 60 are screen shots.
Figure 57:
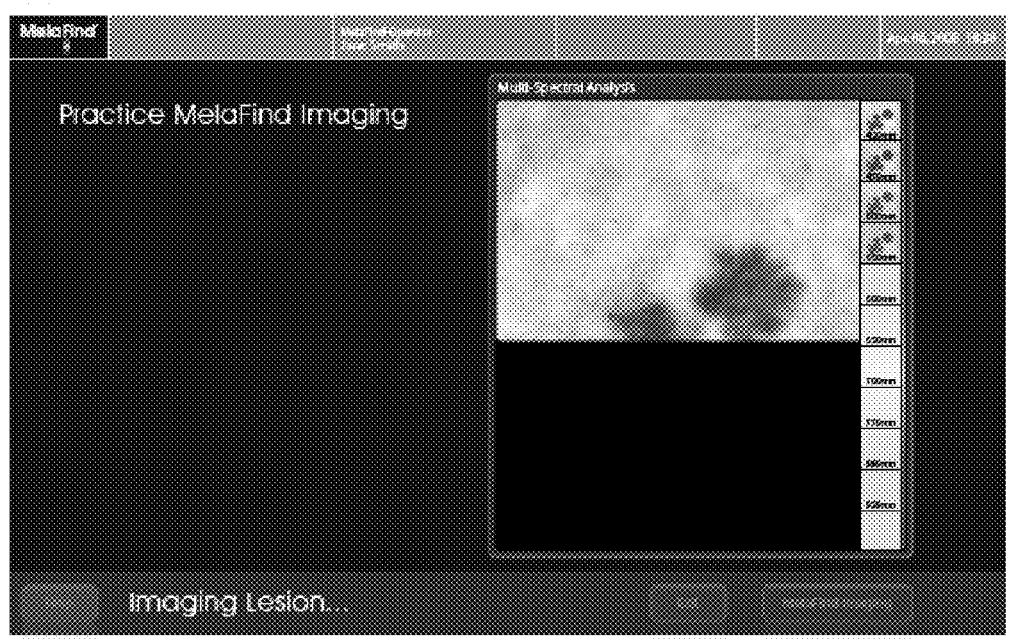

FIGS. 5 through 57 show much larger and fully detailed versions of the same screens that appear as blocks in FIGS. 1 through 4. Each block in each of the FIGS. 1 through 4 has a number 110 below it that identifies the later figure that contains the corresponding larger image of that screen. In addition, each of the later figures includes enlarged portions of the flow lines 104 and the boxes 108.

Turning to the flow to which FIG. 1 pertains, and as shown in FIG. 5, an introductory screen provides text entry boxes 502, 504 for the administrative user to enter the User Name "Admin" and the administration Password. Buttons 506, 508 can be invoked to Log In or Log Out. Successful login leads to the screen of FIG. 6 in which an animation shows to the user that a usage memory card 602 should be inserted in a card reader 604, in the orientation illustrated in the animation. Home and Back buttons 606, 608 return the user to the screen of FIG. 5. Invoking an Admin button 610 leads the user to the screen of FIG. 7.

Figure 6:
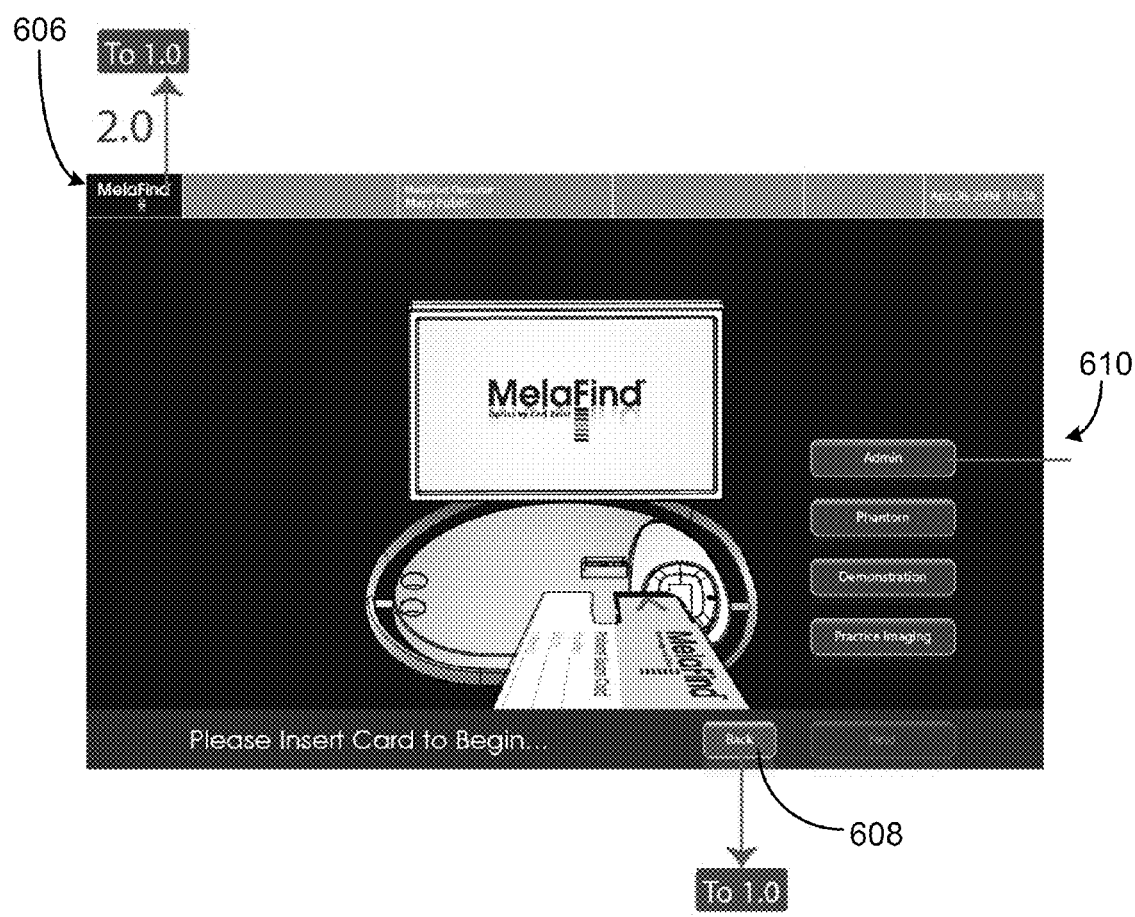
Figure 7:
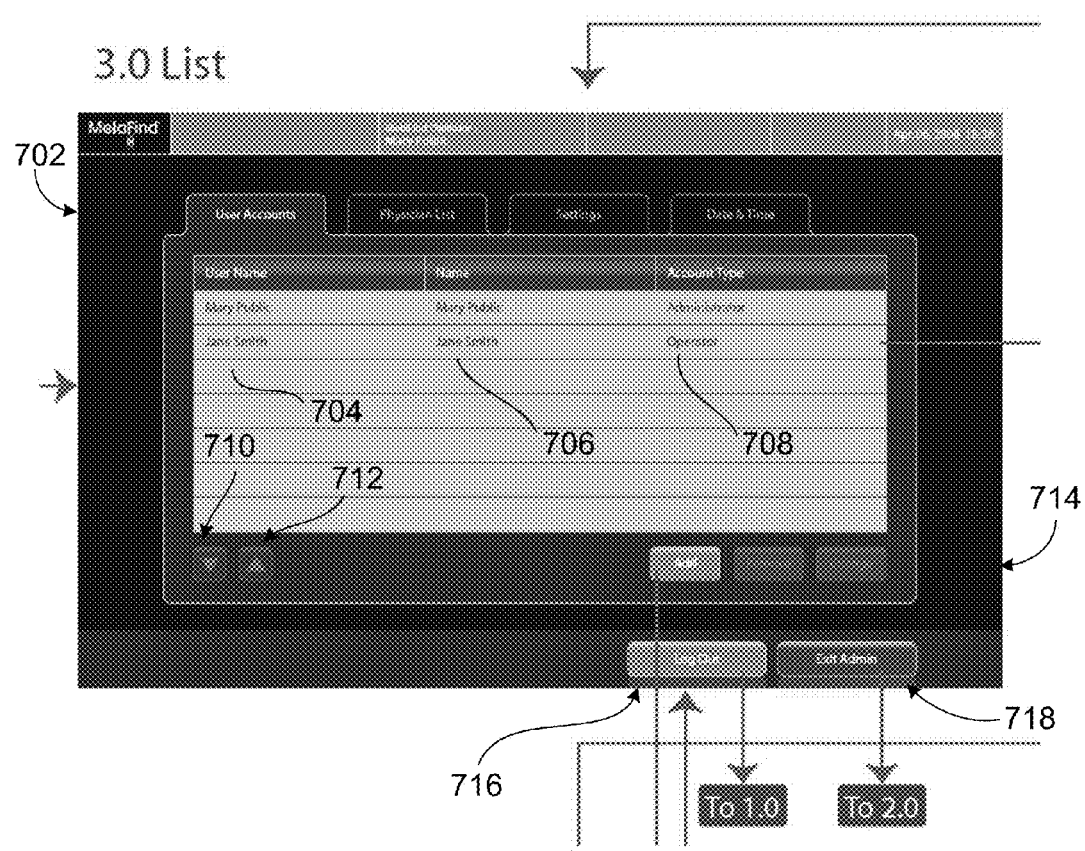

In FIG. 7, each of four tabs 702 can be invoked to direct the user to four other screens that are used for administration. The initial User Account tab screen, shown in FIG. 7, lists User Names 704, Names 706, and Account Type 708. Scroll buttons 710, 712 enable the user to navigate the list if there are more entries than can be shown on a single screen. Buttons 714 can be invoked to enable the user to Add, Remove, or Change a user account. In general in all of the screens discussed with respect to FIG. 1, a Log Out button 716 allows the user to log out, which returns the user to FIG. 5, and an Exit Admin button 718 allows the user to return to the initial administration screen of FIG. 6.

Figure 13:
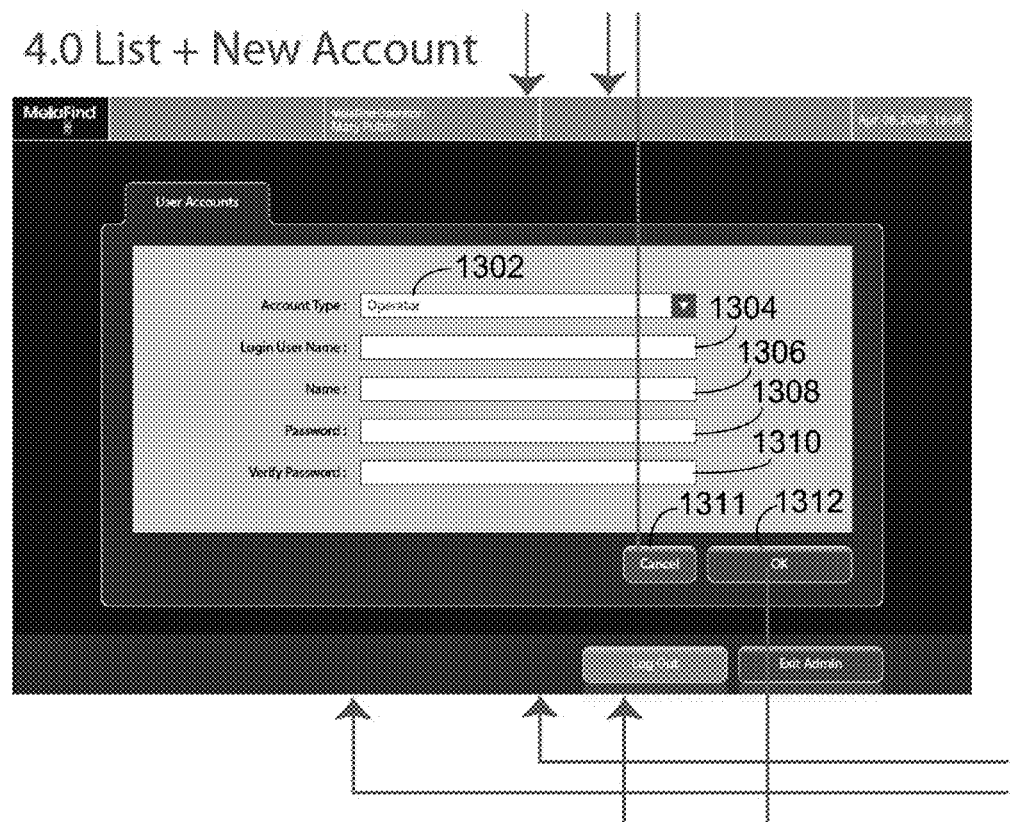
Figure 19:
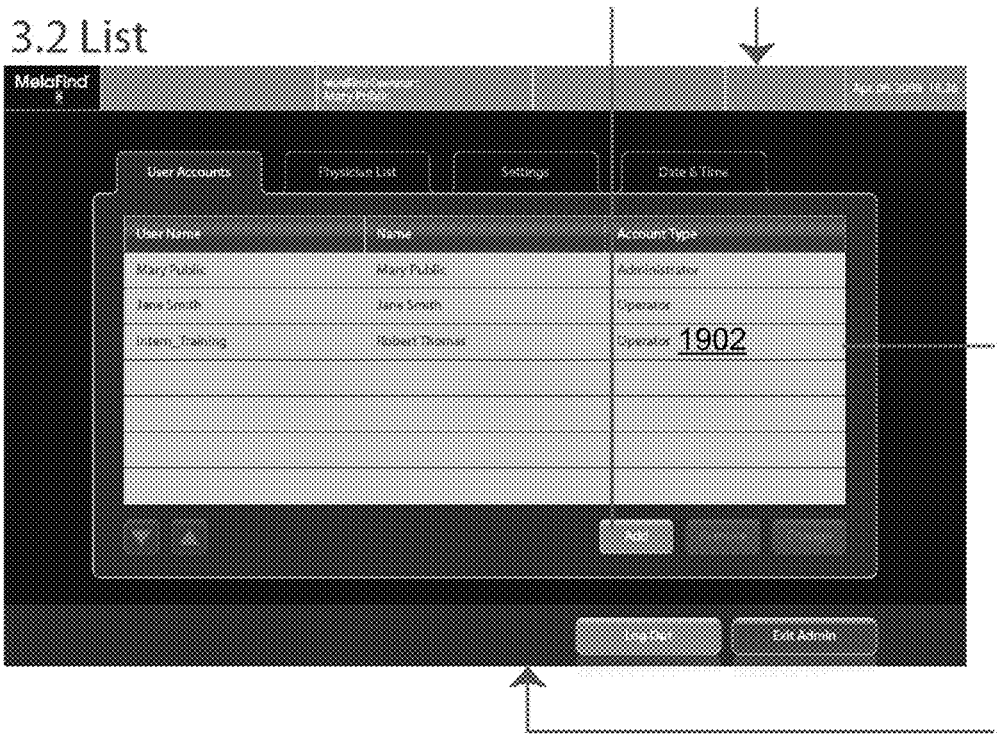

Invoking the Add button 714 leads to FIG. 13, which provides text entry boxes that enable entry of an Account Type 1302, a Login User Name 1304, a Name 1306, a Password 1308, and a verification of the Password 1310. Cancel and OK buttons 1311, 1312 (here and in other figures discussed later) enable the user to commit the entries in the text boxes, or to cancel those entries. Invoking the OK button leads to the screen of FIG. 19 on which the new account has been added. In FIG. 19, and whenever the User Accounts list is displayed, an administrative user can invoke any of the accounts 1902 by clicking on it, which leads to the screen of FIG. 20 on which the selected account is highlighted, and the administrative user can add, remove, or change the account by invoking the buttons 714. The Add button returns the user to the screen of FIG. 13.

Figure 14:
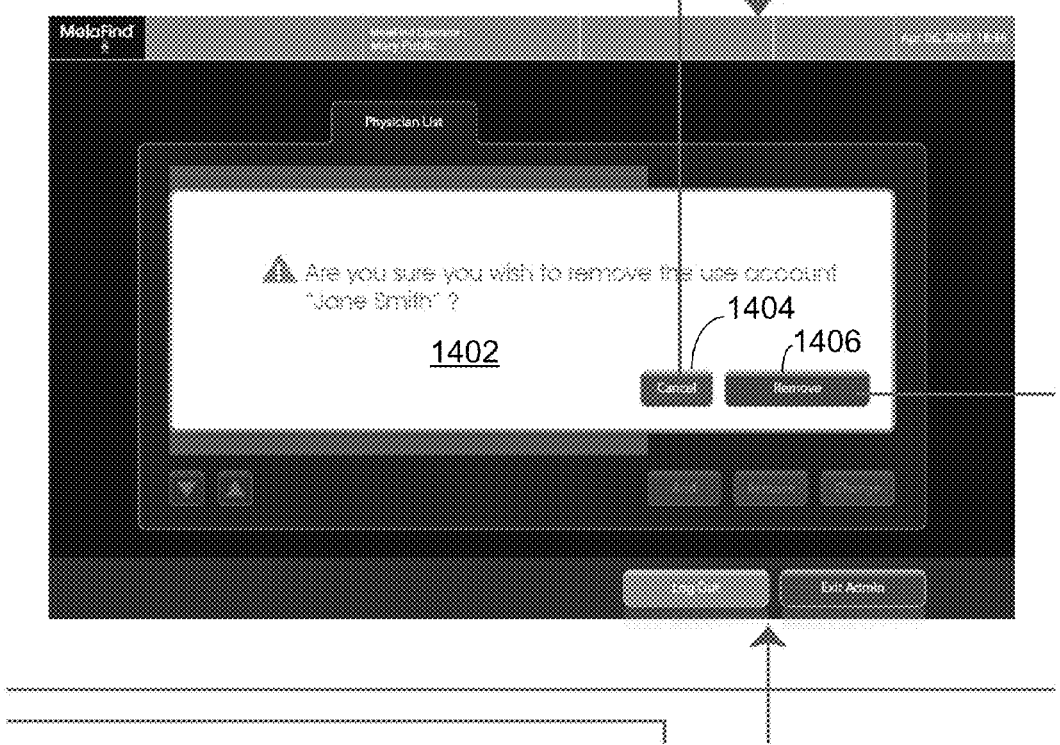

The Remove button 714 returns the user to the screen of FIG. 14, which includes a warning message 1402 and Cancel and Remove buttons 1404, 1406, which here (and in other screens) enable the user to cancel the removal request or confirm the removal. Canceling the removal request leads the user to the screen of FIG. 8; confirming the removal leads to the screen of FIG. 15.

Figure 8:
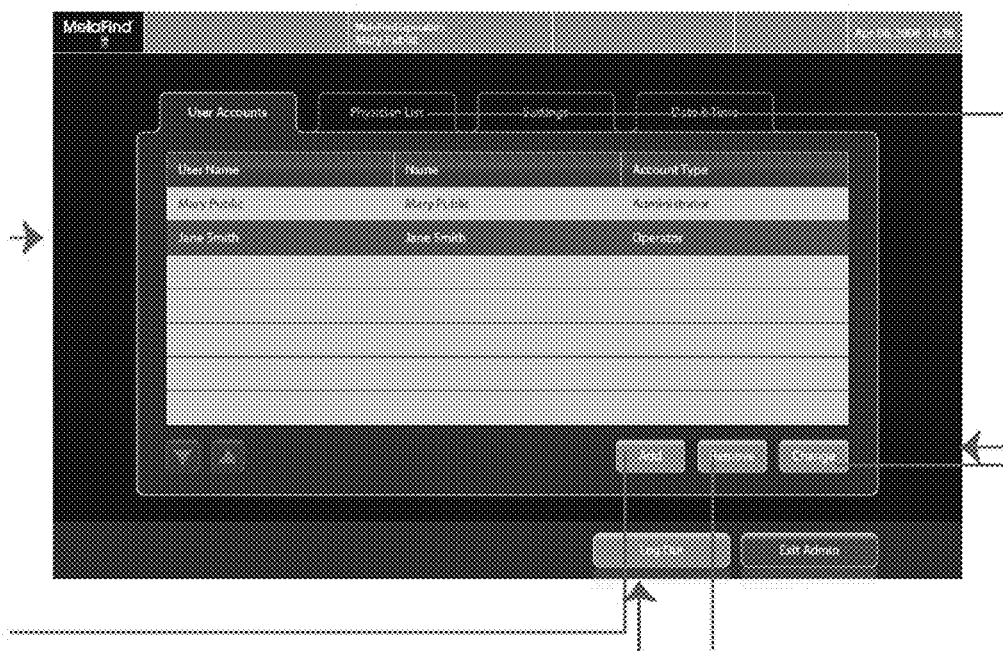

FIG. 8 shows the account list as it was originally. (Note that in FIG. 1, the flow line that connects FIG. 14 to FIG. 8 is with reference to a canceled account addition that occurred through the flow from FIG. 7 to FIG. 8 to FIG. 13 to FIG. 14, and not, in this example, the flow that passed through FIGS. 19 and 20.) FIG. 8 is like FIG. 7 except that the entry that had been considered for removal remains highlighted. The user can again invoke any of the Add, Change, and Remove buttons 714. Invoking the Change button on FIG. 8 leads to the screen of FIG. 9, discussed below.

Figure 15:
Figure 16:
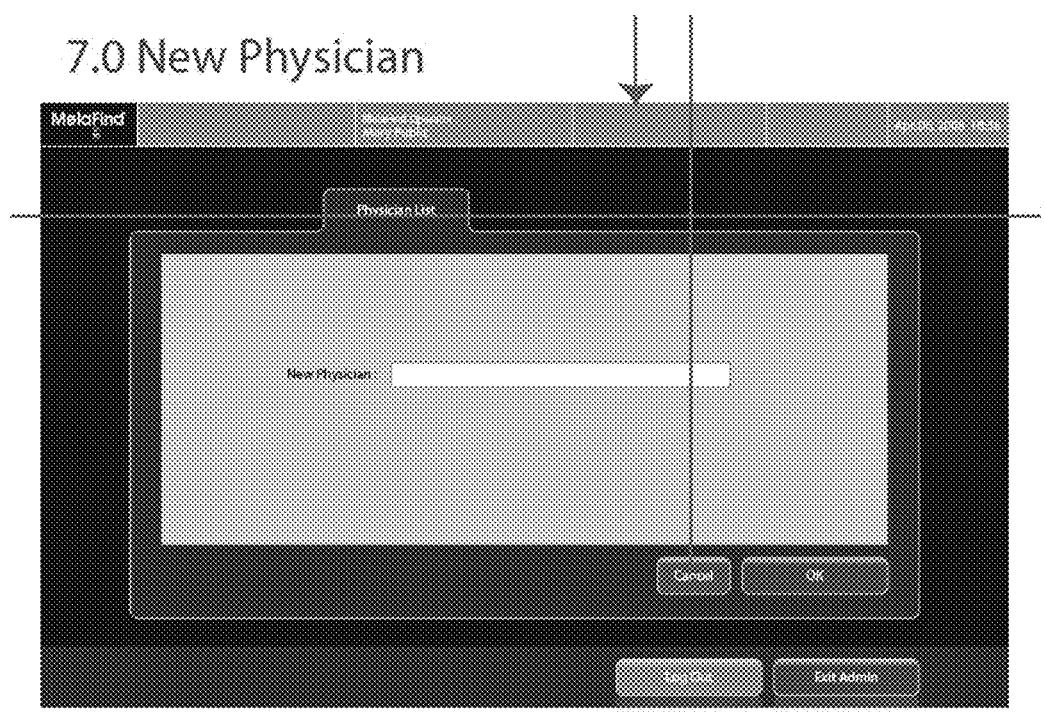
Figure 17:
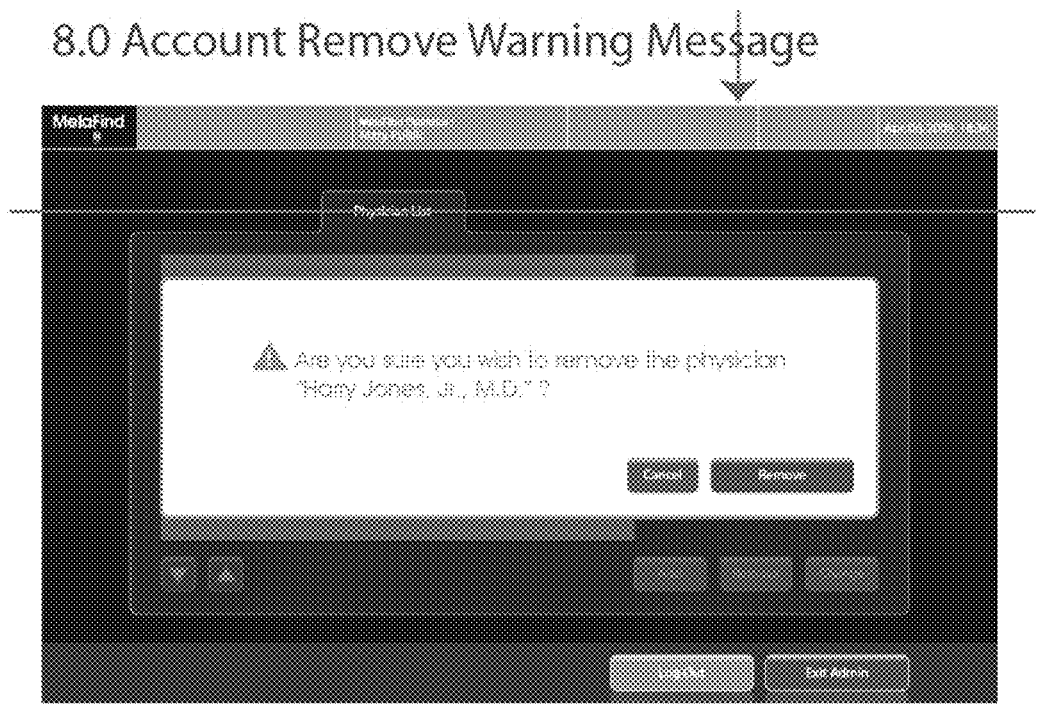

In FIG. 15, which is reached from FIG. 14 by confirming the removal, the account list is shown with the account removed.

Figure 9:
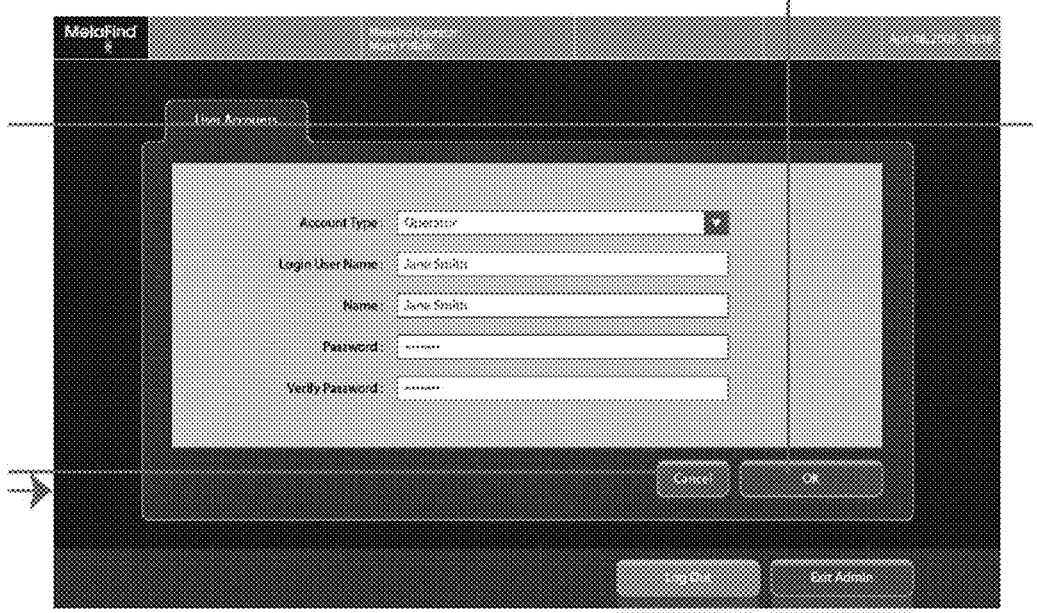
Figure 10:
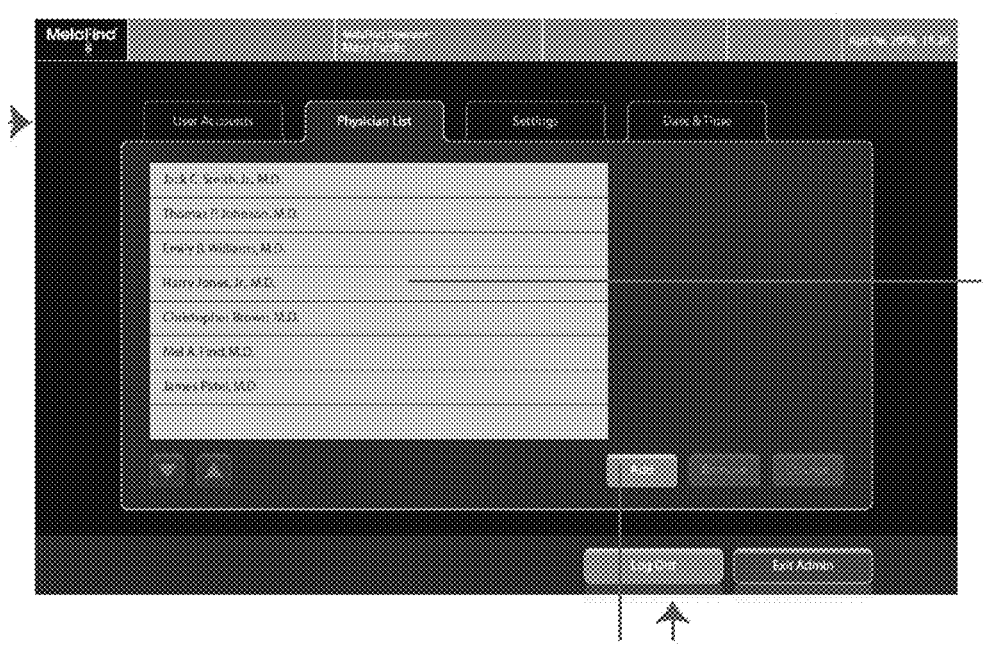
Figure 11:
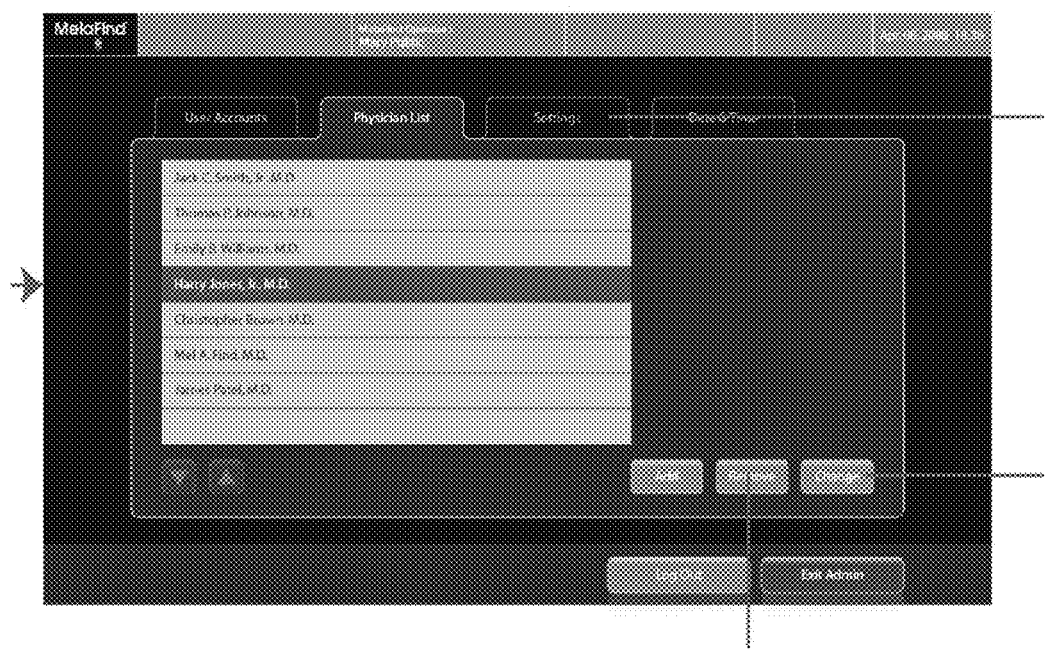
Figure 20:
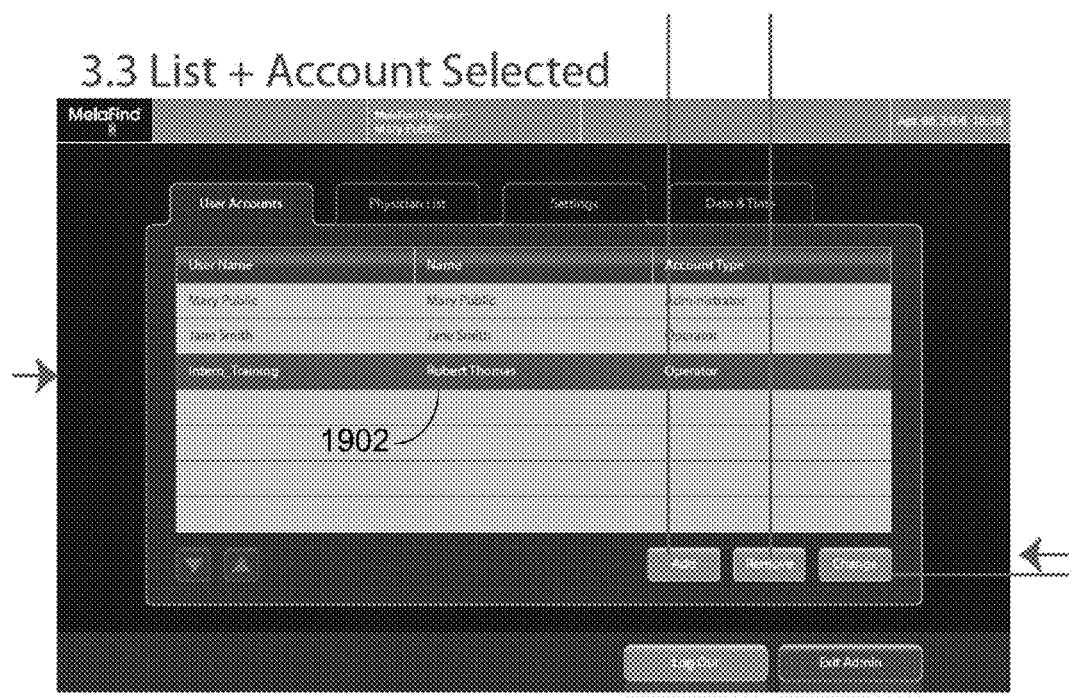
Figure 21:
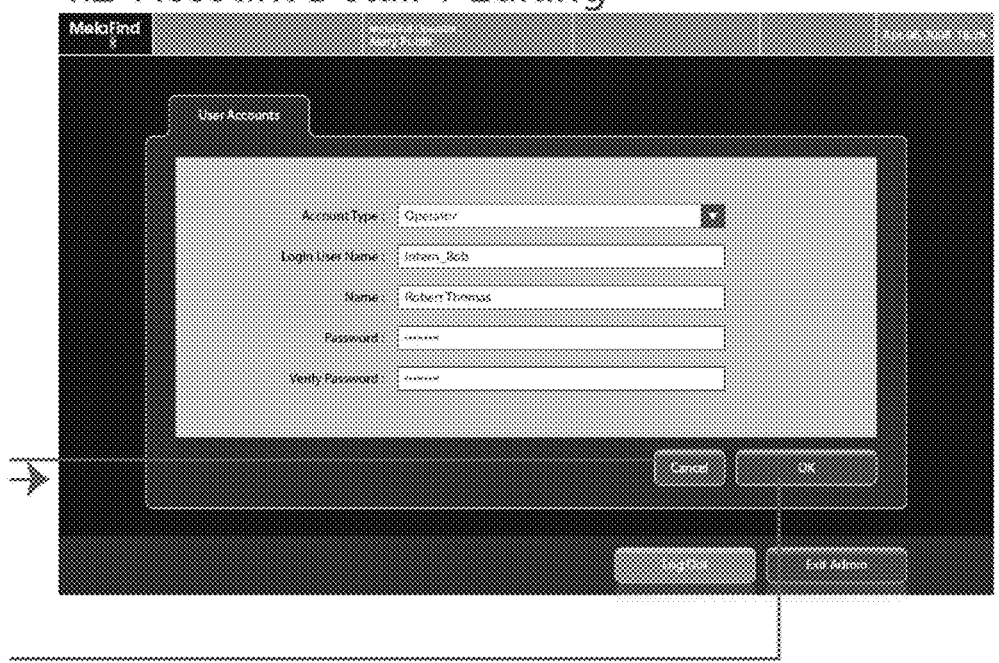
Figure 22:

When an account is to be changed, either from FIG. 8 or from FIG. 20, a screen is shown (FIGS. 9 and 21, respectively) that enables the change information to be entered. (FIGS. 9 and 21 differ because they are reached when the account list is in different states.). In the example of FIG. 9, text boxes are provided for changing any of the items of information that were previously entered in the screen shown in FIG. 13. Invoking the OK button on FIG. 9 returns the user to the account list with the account information changed (FIG. 7). A similar explanation pertains to FIG. 21 with respect to FIG. 19.

FIGS. 10, 11, 16, and 22 provide a similar capability for adding, removing, and changing entries in a list of physician users, all within the Physician List tab.

Figure 12:
Figure 18:
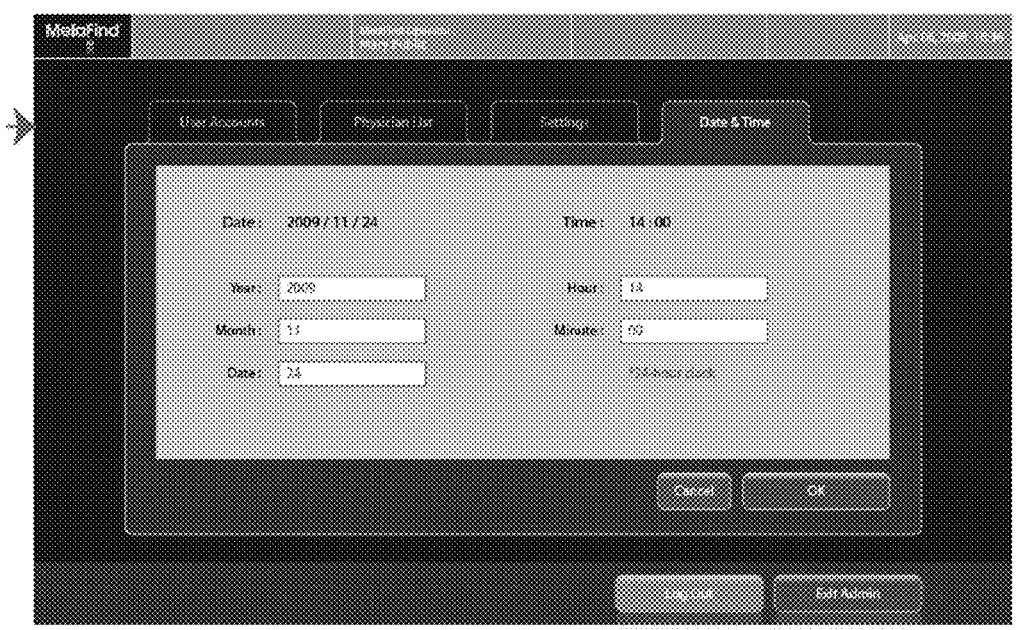

Invoking the Settings tab leads to the screen of FIG. 12 in which the user can use radio buttons 1202 to choose or re-choose when to show results and whether to show a Management Decision. The Date & Time tab, shown in the screen of FIG. 18, shows and allows for resetting of the date and time.

Figure 2:
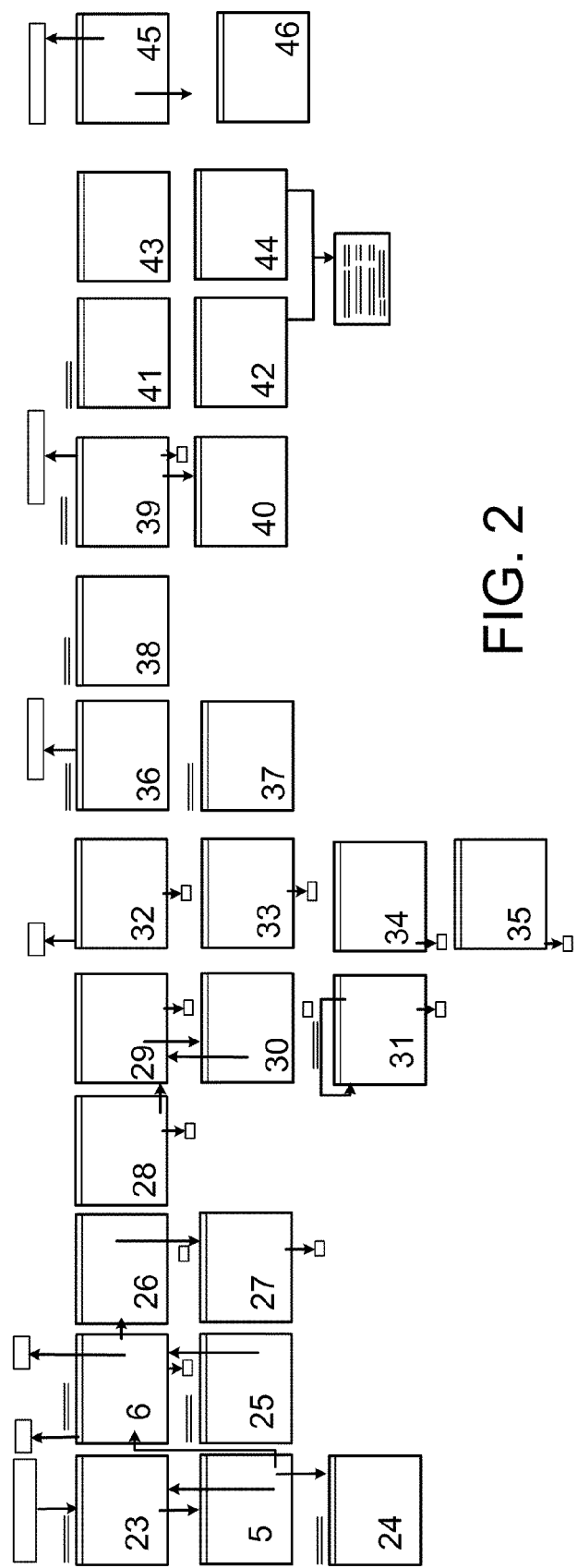
Figure 23:
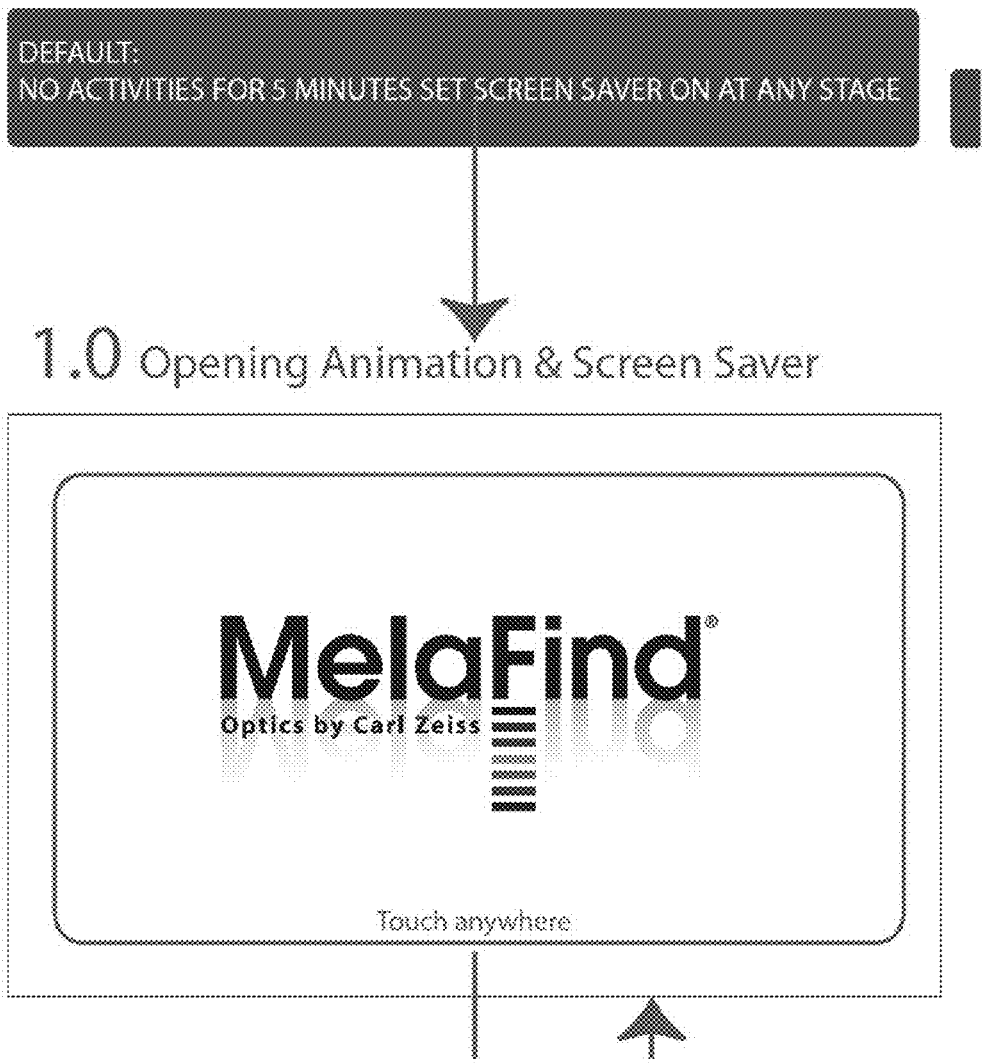
Figure 24:

Turning now to the main user flow shown in FIG. 2, when there has been no activity for a period of time, and when the system is initialized, the screen of FIG. 23 is presented and the user is invited to "Touch anywhere" to begin. Touching the screen leads to the screen of FIG. 5. If the User Name or Password is incorrect, when the Log In button is invoked on the screen of FIG. 5, the screen of FIG. 24 is displayed, and the user can try again. Upon successful login, the screen of FIG. 6 is displayed.

Figure 25:
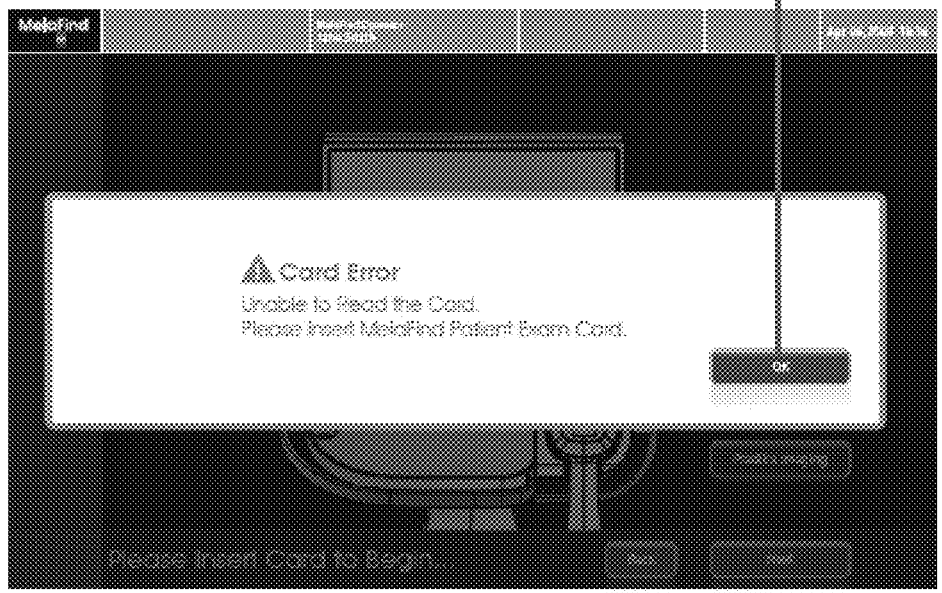
Figure 26:
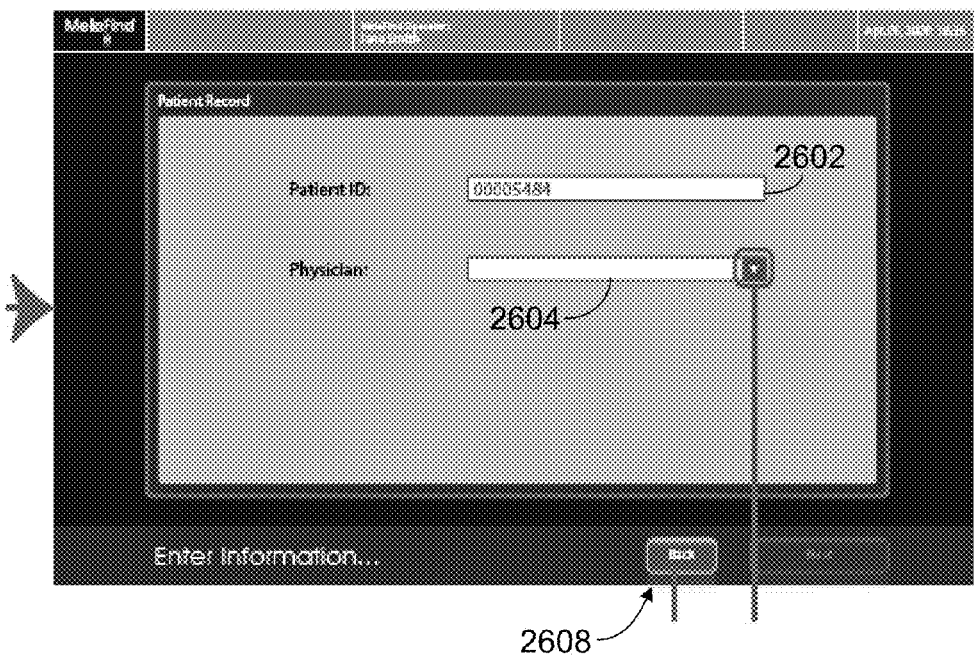
Figure 27:

If the user inserts a card that is not readable or not authorized for use, the screen of FIG. 25 is displayed. The user is warned of the error, and by invoking the OK button can try again. Once a valid readable card has been inserted properly, the screen of FIG. 26 is presented to enable the user to enter an identifier of a patient in a Patient ID text entry box 2602 and to identify a physician using a Physician drop down box 2604, which leads to the screen of FIG. 27, where a physician is chosen, and then to the screen of FIG. 28 in which the selected physician is displayed. If the inserted card is one that had been used previously, the patient ID is read from the card and displayed in FIG. 26. If the inserted card is a new one, the user can enter a patient ID which is then written onto the card. FIG. 2 does not include explicit flow lines that connect a screen to the next screen that appears when the user invokes the Next button. Generally, the next screen is the one to the right of the current screen or in the column next to the right, and the flow line or lines are implicit.

FIG. 26, and other figures associated with the flow of FIG. 2 include a Back button 2608 which returns the user to the previous screen, and a Next button 2610 which causes the next screen in the sequence to be displayed.

Figure 28:
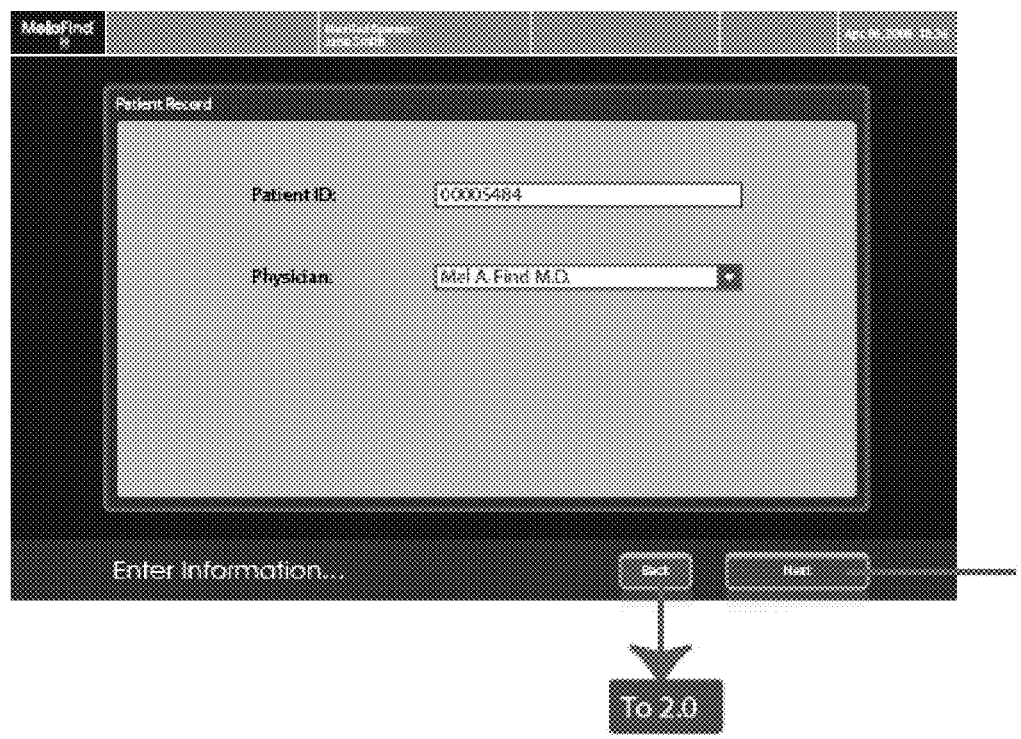
Figure 29:
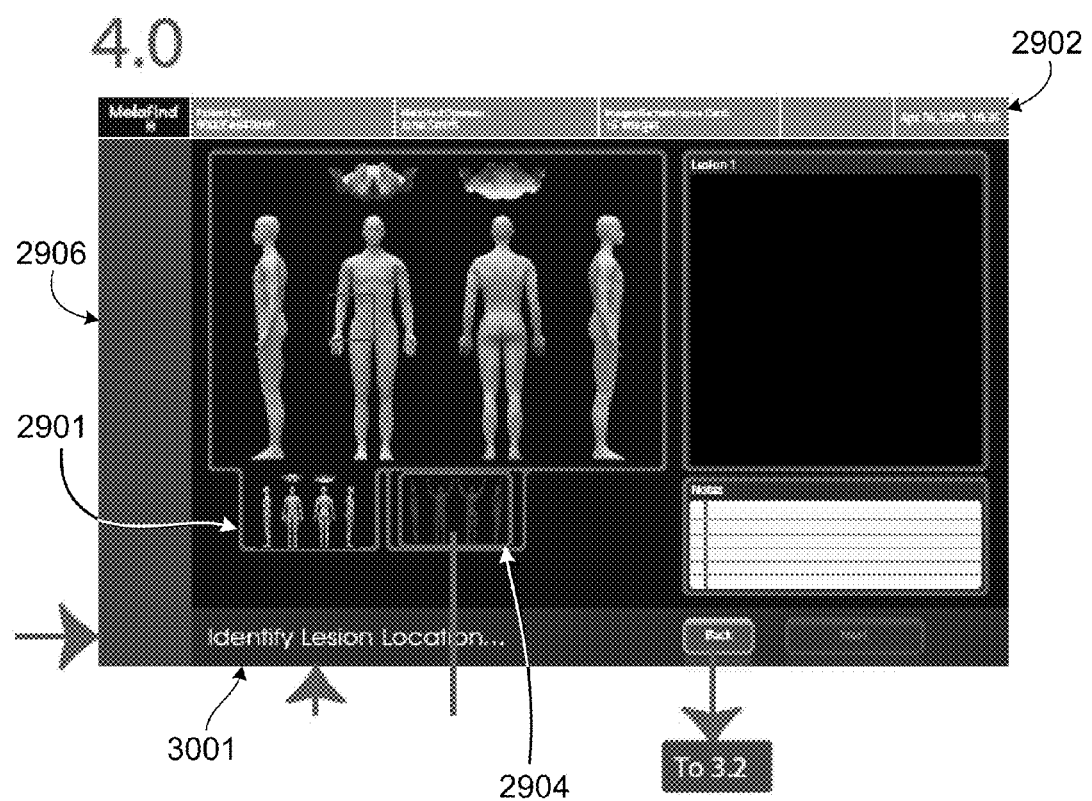

FIG. 29 shows the next screen after FIG. 28. The screens of FIGS. 29 through 44 provide a simple-to-use and very powerful navigational and informational interface for the user to understand, observe, use, and provide information about the lesions associated with the patient and to acquire scans of new lesions. On each of these screens a banner 2902 at the top identifies the patient ID, the user's name, the number of remaining images of skin lesion scans that can be added to the card, and the current date and time. In general, all of the screens of the user interface include the banner 2902 and the information shown on the banner varies depending on the state of the interface.

Figure 30:
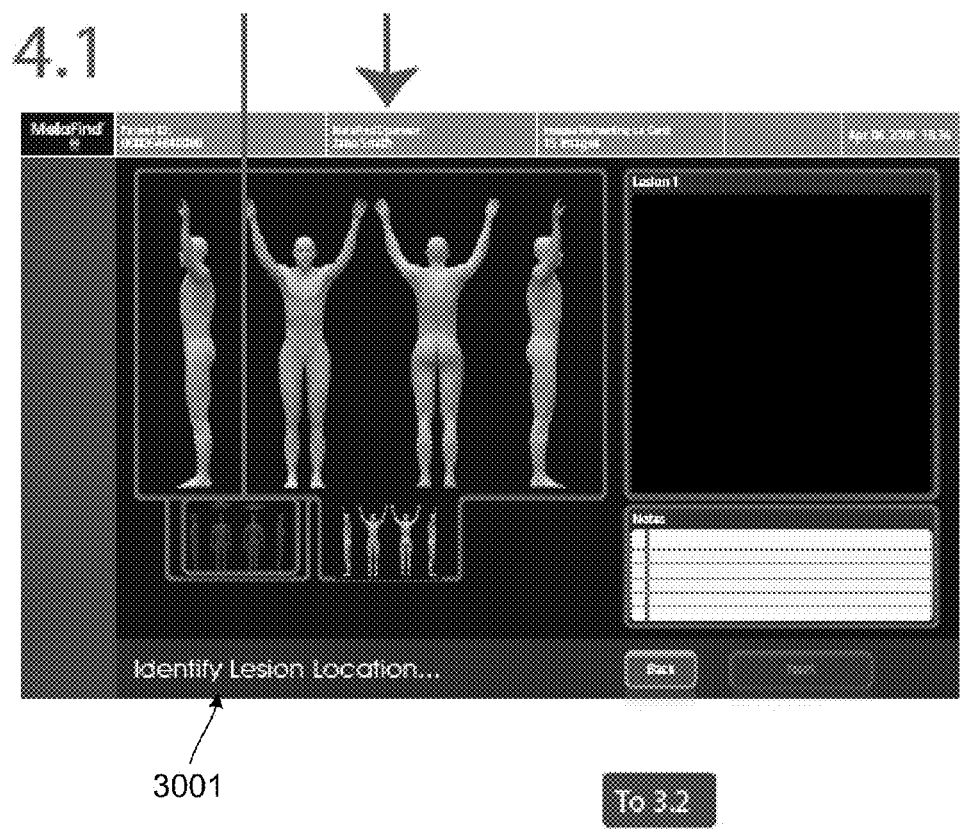
Figure 31:
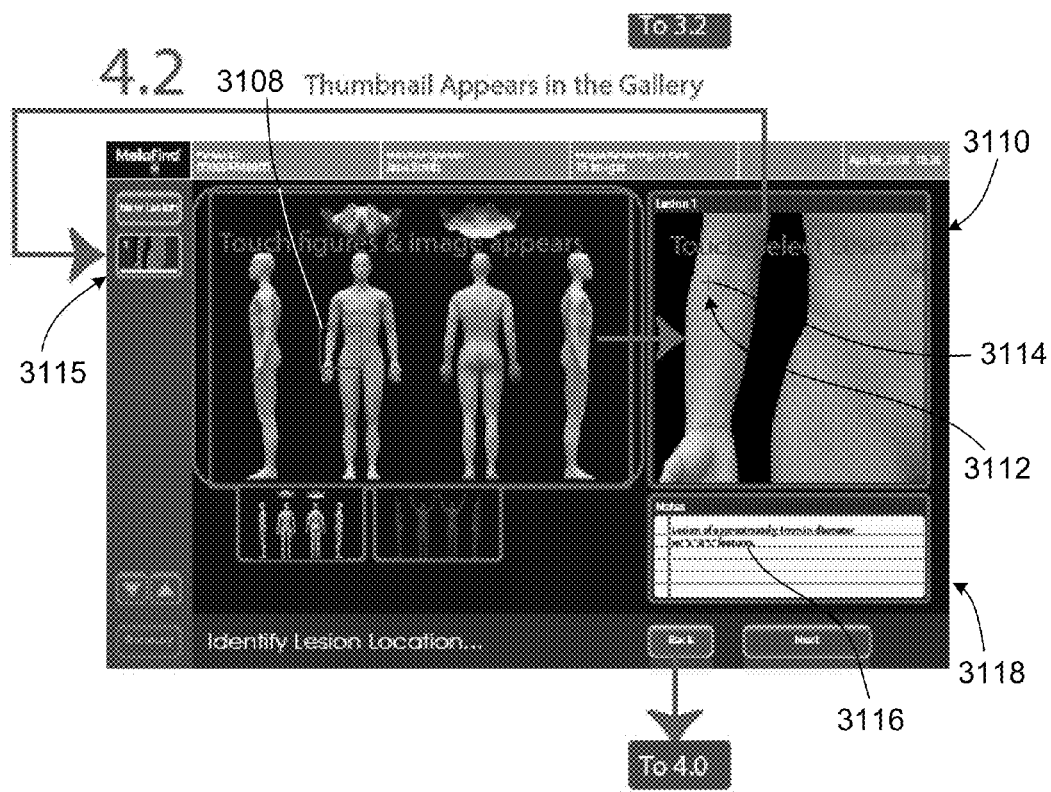

There are three types of screens represented in the group of FIGS. 29 through 44. The screens of FIGS. 29 through 31 are scan preparation screens that enable the user to identify the locations of (and enter notes concerning) lesions that are to be scanned on the patient. The legend 3001 at the bottom of the screens provides instructions and guidance to the user about the function to be performed on the screen (and this also is true of other screens discussed above and below). For example, on the screens of FIGS. 29 through 31, the legend 3001 provides the instruction "Identify Lesion Location . . . " to alert that user to use these screens to point out the location of a lesion that is going to be scanned.

In the screen of FIG. 29, for example, there are two viewing tabs 2901 and 2904. Tab 2901 bears thumbnail images of a body of a model viewed from six different perspectives: top (looking straight down on the head), bottom (looking straight up at the bottoms of the feet), left side, right side, front, and back. The main part 2906 of the tab 2901 shows larger versions of the six views. The tab 2904 similarly has four thumbnail and larger views, left, right, front, and back, of the model with arms raised, so that parts of the body not visible in tab 2901 are visible in tab 2904. When a tab has been invoked the thumbnail views are visible, and when the tab has not been invoked the thumbnail views are grayed. The screen of FIG. 30 is shown when tab 2904 is invoked.

Figure 58:
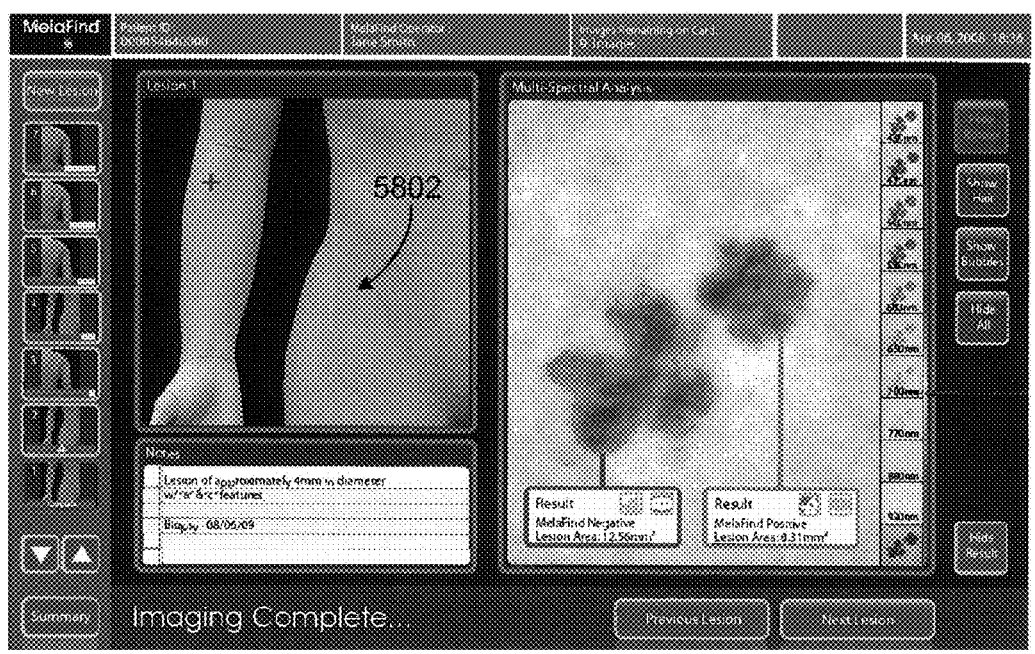

The human model views of FIG. 29 and other figures discussed below are arranged to represent a real human of either sex. In particular, certain sex-related features of the body, such as the genitals, are not shown explicitly, but instead are replaced by a smooth surface that can be interpreted as belonging to either sex. Hair is not shown on the model, which enables lesions to be identified and shown on parts of a real human that are normally obscured by hair, such as a lesion in the pubic region of the body, or on a bearded face or on top of the head. In addition, the absence of hair contributes to the impression that the model could represent a real human of either sex. The human model is constructed digitally and is not a photograph of a real human. Thus, the surfaces, symmetry, body build, proportions, shape, and size of the human model are stylized. As shown in FIG. 58 (and other figures, in which this feature may not be apparent because the lines are fine), a grid 5802 of generally vertical and horizontal lines is shown on the surface of the human model. These lines can be used as a basis for identifying the precise locations of lesions on a real human and displaying those locations accurately on the human model, among other things.

On the left side of the screen of FIG. 31 (and other figures) a lesion navigation pane 3102 is displayed that includes thumbnail images 3103 identifying locations of lesions on this patient, and triangular up and down scroll buttons 3104, 3106, that enable a user to scroll up and down to find a lesion of interest if not all thumbnails will fit in the pane. When a new lesion is to be scanned on the patient by the user of the interface, a New Lesion button 3108 is displayed. Invoking the New Lesion button enables the user to indicate the location on the body of the patient of the lesion that has been scanned, by using the model that is displayed in model tabs 2901, 2904.

In FIG. 31, if the user touches a location 3108 on one of the views of the model, the lesion location pane 3110 shows an enlarged, close-up view of the portion of the model that was touched. Next, the user can touch a location 3112 in pane 3110 to indicate the location of the scan. A marker 3114 is then displayed at the location of the lesion. In addition a corresponding thumbnail 3115 is placed in the lesion navigation pane. The user can enter text Notes 3116 in a text pane 3118 that may identify, describe, or otherwise relate to the lesion. The content of the notes pane is linked to and synchronized with the image in the lesion pane, the lesion navigation pane, and the viewing tabs, for display purposes.

A second set of the screens, in FIGS. 32 through 40, include the lesion navigation pane on the left, and have the lesion pane and the notes pane relocated to the left. These screens enable a user to prepare for and then acquire a new scan of a skin lesion of the patient, for example, at the location identified in FIG. 31.

Figure 32:
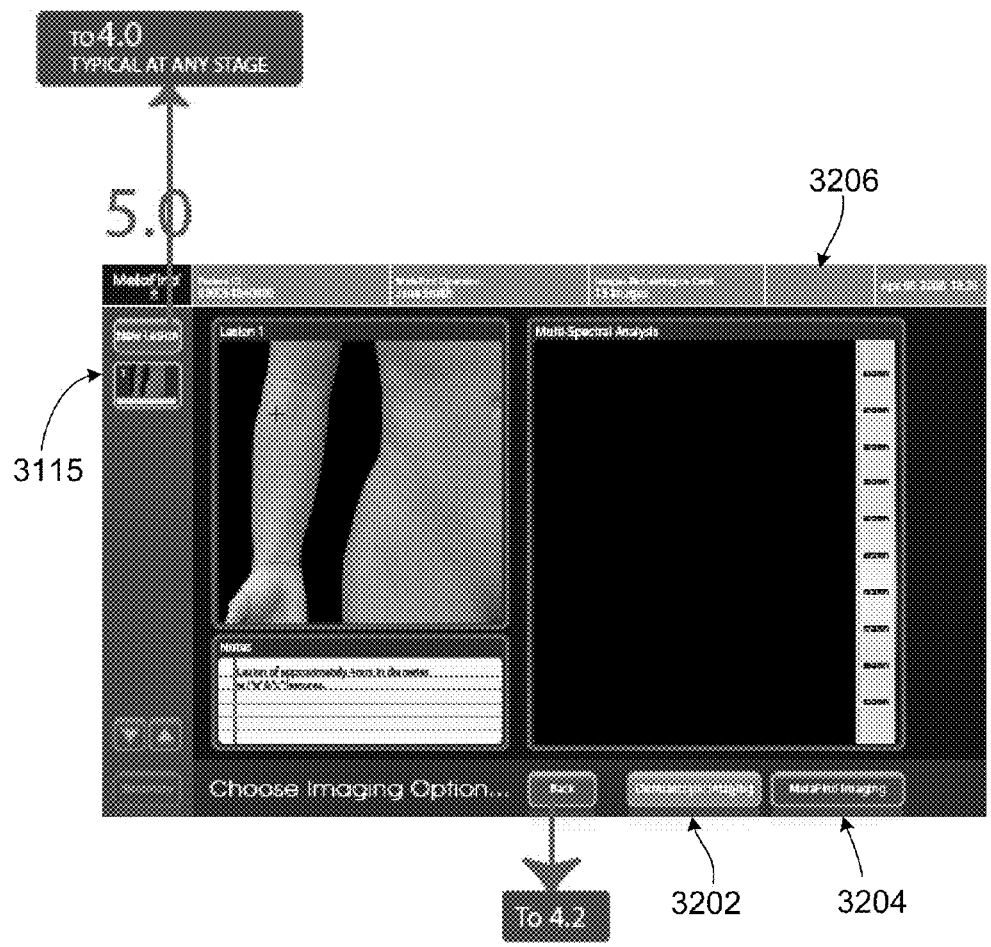

In the example as shown in FIGS. 31 and 32, the user has identified a location at which a new lesion will be scanned. The location is represented on the lesion thumbnail 3115 and on the enlarged view of the model in the lesion location pane using a cross hair marker in red. Typical notes concerning the lesion are shown in the notes pane, and the notes can be edited. The user may invoke either of two Imaging Option buttons 3202 and 3204, to indicate that the user wishes to acquire a scan of the lesion at that location either using a dermascope (Dermascopic Imaging) or a hand-held MelaFind probe (MelaFind Imaging). Although in this discussion we refer to the possibility of dermascopic imaging and to the display of the results of such imaging, in some implementations of the user interface, dermascopic imaging might not be enabled, in which case dermascopic images would not be displayed. In some other implementations, images acquired with the MelaFind probe could be displayed in a "Dermascopic Imaging" mode.

Figure 33:
Figure 34:

Once the user has identified the location of the lesion, the screen of FIG. 32 advises the user to choose an imaging option. After one or the other of the buttons 3202, 3204 is invoked, the screen of FIG. 33 is displayed, which invites the user, in the message in the legend 3001 at the bottom of the screen, to use the hand-held scanner to scan the lesion. When the user begins the scan, the screen of FIG. 34 is displayed with the message "Imaging Lesion." FIG. 34 shows a portion 3208 of an image of a lesion in a Multispectral Analysis pane 3206 on the right side of the screen. During scanning a progress bar 3430 under the thumbnail for the lesion being scanned shows progress toward completion of the scanning process.

On the right side of the multispectral analysis pane 3206 a column 3210 of thumbnail positions 3211 represents a succession of spectral bands for which spectral-band images are taken, for example, when the MelaFind probe is used to scan a lesion. Each of the thumbnail positions represents the spectral-band image for one of the spectral bands. The presence of a thumbnail 3212 in one of the positions in the column indicates that the corresponding spectral-band image has been acquired for that band. The summary button 3214 on the screen of FIG. 34 (and on other screens) enables the user to move to a screen, such as the one shown in FIG. 41, that provides a summary of scans stored on the memory card for this patient.

Figure 35:
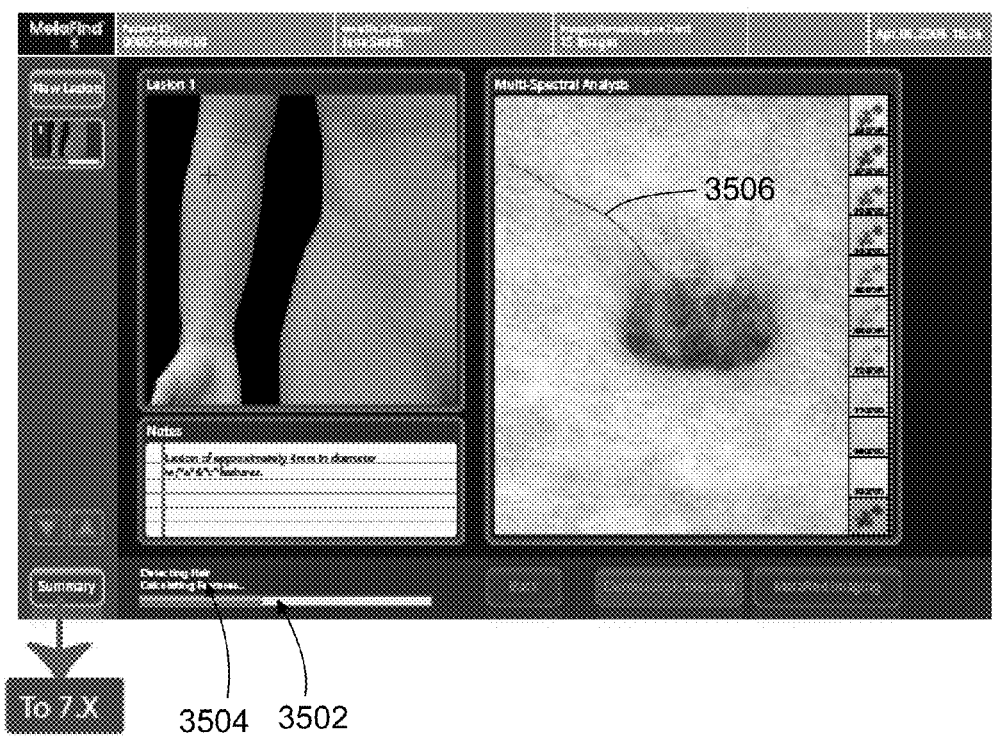

The scan of FIG. 35 shows a state in which scanning has been completed and the scanned images are being processed. The progress toward completing the image processing is indicated in a progress bar 3502 as well as in the lesion thumbnail and a legend 3504 above the bar indicates the step that is being performed, in this case "Detecting Hair; Calculating Features . . . " In this instance, the hair being detected is highlighted 3506 in the multispectral analysis pane. Because the scanning has been completed, all of the thumbnail positions in the column 3210 contain thumbnails, and the bottom position in the column shows a thumbnail of the "full-spectrum" (reconstructed color) image.

Figure 36:
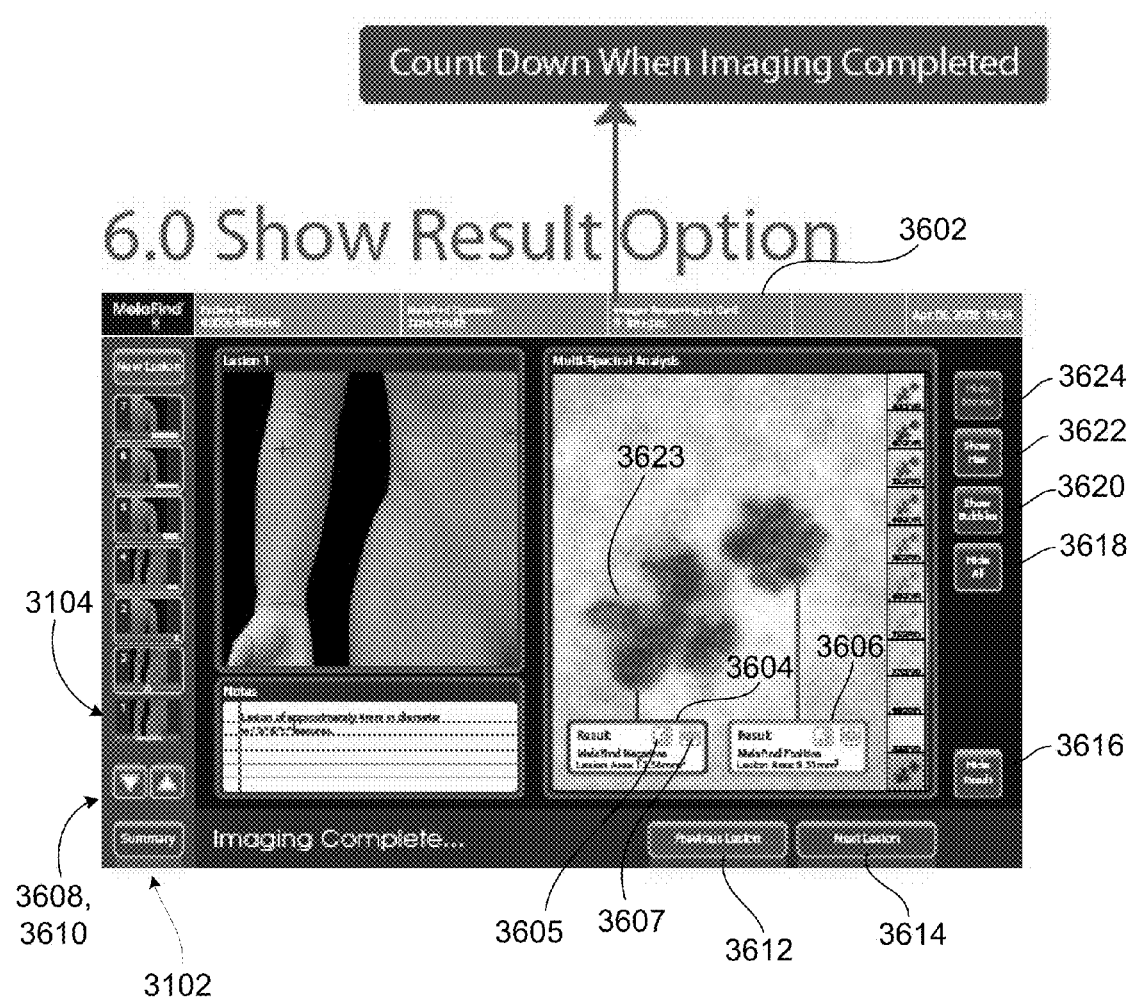

When the image processing has been completed, the screen of FIG. 36 is displayed, including the legend 3001 "Imaging Complete . . . " Thumbnails of other images that have been scanned now also appear in pane 3102.

In addition, results of the most recently completed scan are shown in text boxes such as 3604, 3606 in the multi-spectral analysis pane. In this instance, the scan contained two different lesions, which were analyzed separately, and are both included in the image of the scan. The result for the left lesion is "MelaFind Negative" and the lesion area is reported in square millimeters. The result for the right lesion is "MelaFind Positive" indicating a recommendation that a biopsy be performed. These results (positive or negative, indicating the need to biopsy or not) are of the kind described or referred to in U.S. patent application Ser. No. 11/761,816, filed Jun. 12, 2007; Ser. No. 11/681,345, filed Mar. 2, 2007; Ser. No. 11/956,918, filed Dec. 4, 2007; and Ser. No. 12/512,895, filed Jul. 30, 2009, all of which are incorporated here by reference. In each of the Result boxes, one of two icons 3605, 3607 is highlighted to indicate either that the lesion should be biopsied (microscope icon) or that it should be observed (eye icon). The Result boxes are displayed directly on the scanned image in this example, but could also be displayed in a wide variety of other ways.

The completion of the image processing for a scan, as represented in the screen of FIG. 36, and the storage of the images and related data on the memory card completes the scan and represents a usage (or depletion) of one of the available scans on the memory card. The number of Images Remaining on the card, shown in the entry 3602, is reduced by 1, in this case to "9 images". This message alerts the user to how many additional scans can be stored on the memory card for this patient, before another card needs to be used.

Also, with the completion of image processing for the current scan, the general state of the screen is changed so that it is no longer in a scanning mode, as discussed above, but is now in a lesion navigation mode. In the lesion navigation mode, the screen elements are arranged to enable a user to navigate easily from one of the scanned lesions to another and therefore to view the images of different lesions, the multi-spectral images for each lesion, and the results of the analysis of each lesion, among other things.

In the lesion navigation mode, the lesion navigation pane 3102 is updated to show thumbnails of all of the lesions that have been successfully scanned, processed, and stored on the memory card. The scroll buttons 3608, 3610 become brighter and are active to permit easy navigation, and the user can invoke any of the lesion thumbnails in the pane, which then is highlighted to indicate that it has been invoked. (In general, when a user control is displayed more brightly on any of the screens, that control is active and can be invoked, and when it is displayed less brightly ("greyed"), it is inactive and cannot be invoked.)

In the lesion navigation mode, as shown in FIG. 36, and enlarged in FIG. 58, additional user controls are displayed, including Previous Lesion and Next Lesion buttons 3612, 3614, which enable the user to quickly move back and forth in the sequence of stored lesions. A Hide Result button 3616 can be toggled to show or hide the Result text boxes 3604, 3606. Artifacts of the images and viewing aids can be shown or hidden by toggling the Show/Hide Border button 3624 (which toggles the border 3623 shown around each lesion corresponding to the border that was used to define the lesion for image processing purposes); the Show/Hide Hair button 3622, the Show/Hide Bubbles button 3620, and the Show/Hide All button 3618. A Show/Hide Result button 3616 enables toggling between showing the Result text boxes or hiding them.

Figure 37:
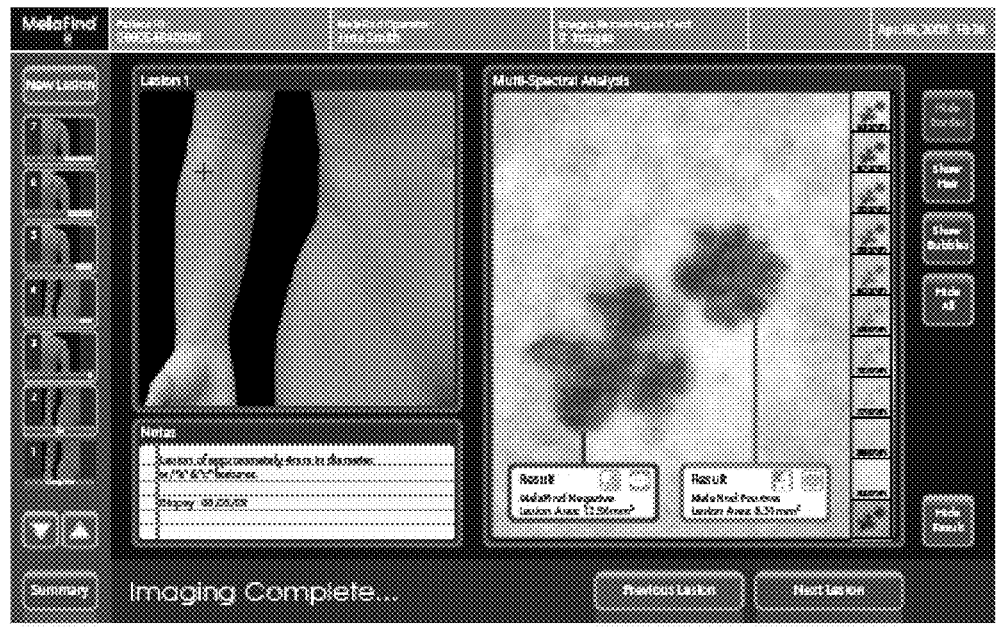
Figure 38:
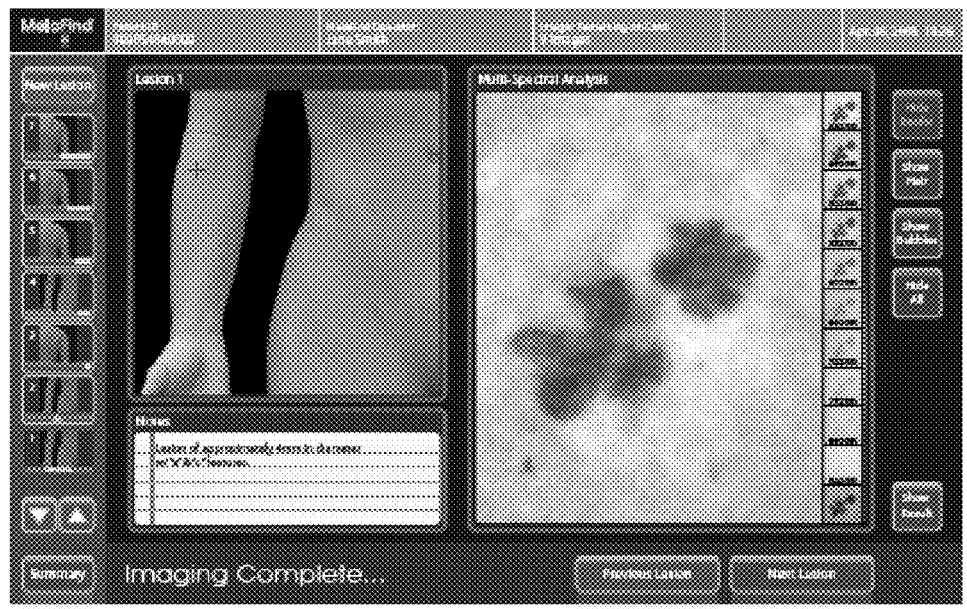

The screen of FIG. 37 is like the screen of FIG. 36 except for the addition by the user of a "Biopsy" note in the Notes pane. The screen of FIG. 38 is similar, but the results are hidden.

Figure 39:
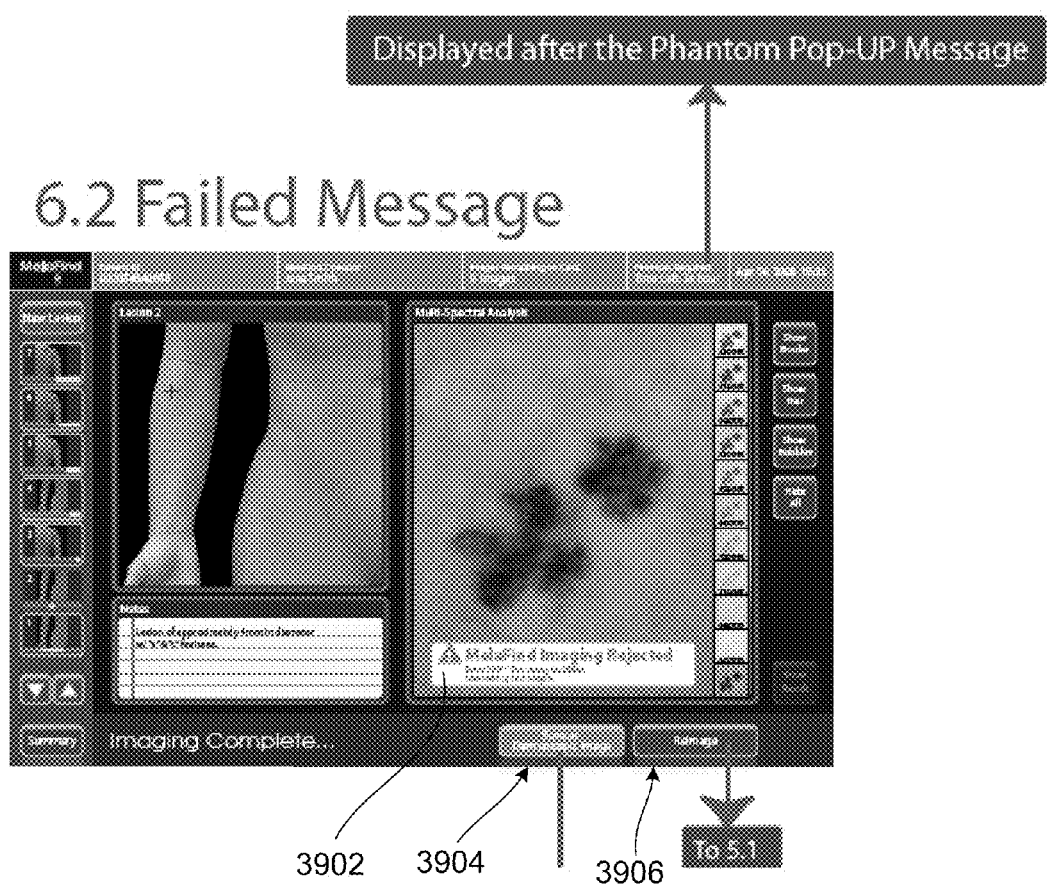

In some cases, the scan attempted by the user fails because the image analysis cannot be done effectively with an appropriate degree of confidence. The screen of FIG. 39 is then displayed to the user, including an error message 3902, which indicates the existence of the error and provides an explanation, in this case "Too many bubbles. Use rolling technique." The screen also includes a "Save as Dermascopic Image" button 3904 (which enables the user to save the image but without the results of image analysis) and a ReImage button 3906 (which allows the user to restart the imaging process for the identified lesion).

Figure 40:
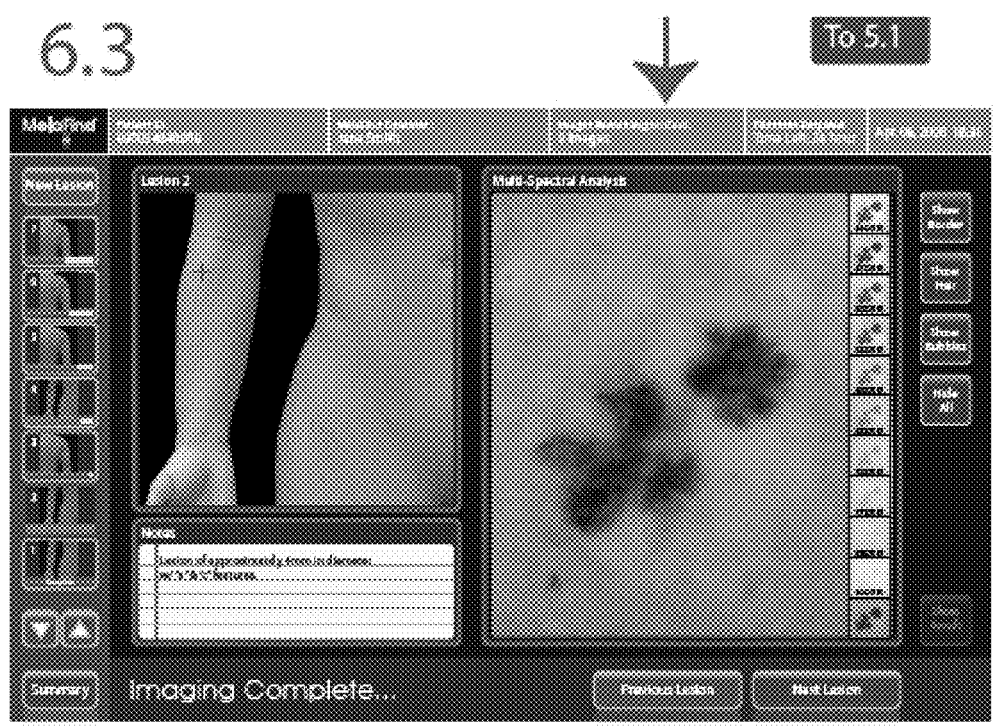
Figure 41:
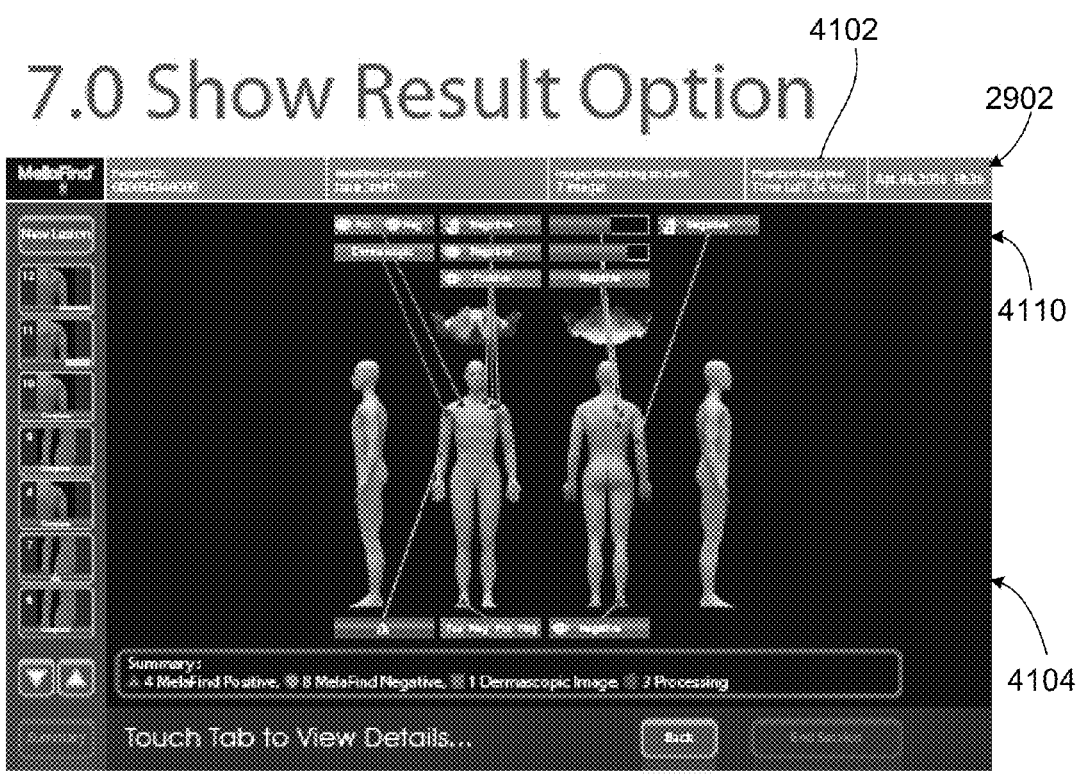

As illustrated by the screen of FIG. 40, the user can use the thumbnails in the column on the right side of the Multi-Spectral Analysis pane to select and view the full-spectrum image (as is the case in FIG. 40) or any of the spectral-band images. This enables the user to observe, understand, and develop an instinctual understanding for the relationship between the result being displayed and the characteristics of the various spectral-band images associated with that result.

The screens of FIGS. 41 through 44 are the summary screens that enable the user to view, using the model and the lesion navigation pane, all of the scans and results for all of the imaged lesions of the patient. In other words, these screens present an easily navigable overview of the scanned skin lesion situation for this patient. In all of these screens, the banner 2902 includes an alert 4102 that informs the user how much time is left before a scan must be done of a phantom target so as to enable a "Self-Test" of the probe functionality.

Figure 42:
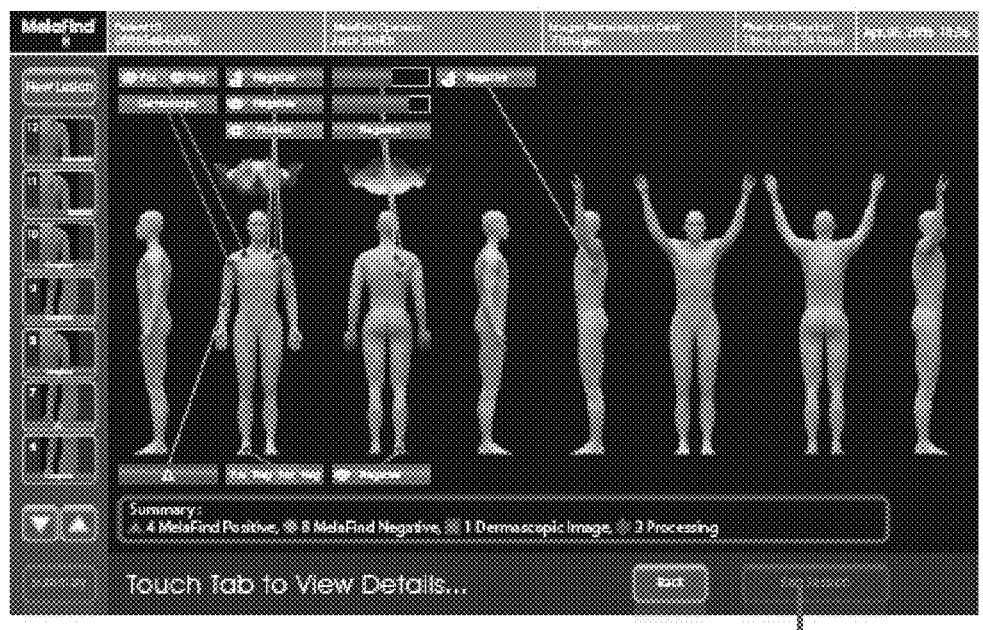
Figure 43:
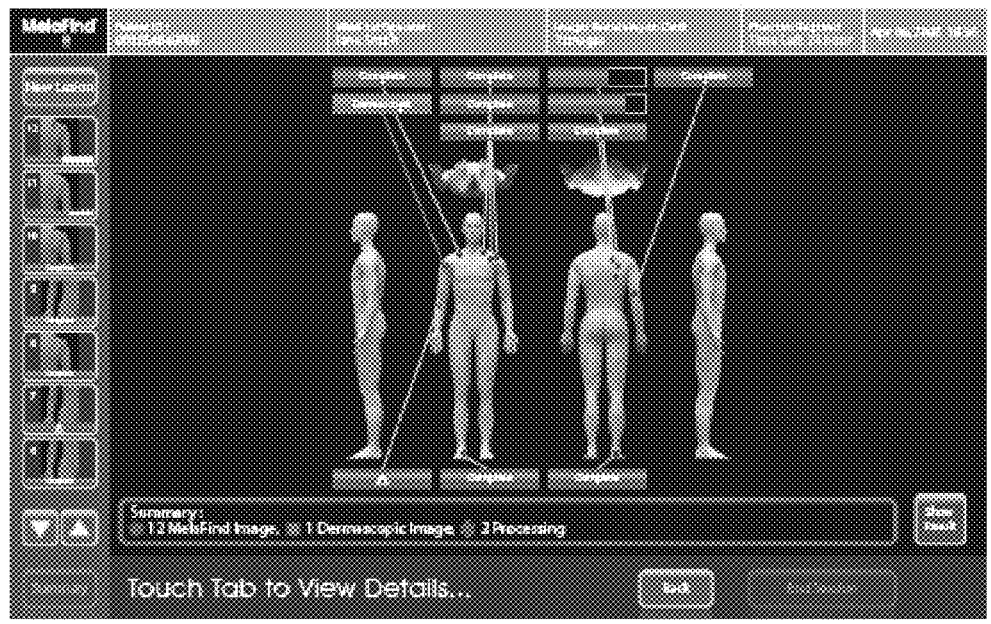

In the example screens of FIGS. 41 through 44, a summary bar 4104 illustrates (using a color key and different symbol shapes) the number of lesions of each of four types: MelaFind Positive, MelaFind Negative, Dermascopic, and images that still are in the state of Processing. In other implementations, not illustrated here, the "Dermascopic" type could either be absent or replaced by another type. A Show/Hide Result button 4302 (see FIG. 43) is used to toggle the screens between one state in which MelaFind results are shown (FIG. 41 for example), and a second state in which they are not (FIG. 43, for example).

The colors and symbol shapes in the summary bar correspond to symbol shapes and colors on lesion status bars 4110. There is a status bar shown for each lesion. In this case, there are twelve bars corresponding to twelve lesions that were scanned. In this example, a green eye is used to indicate that the next step is observation and a red microscope is used to indicate that the next step is biopsy. Blue is used to indicate that computer processing is not yet complete. In this example, purple identifies a dermascopic image. Progress indications are shown also in the lesion thumbnails. A wide variety of other colors and icons could be used.

In the Show-Results state, each lesion status bar has a color that corresponds to the status of the lesion (in the example shown: positive, negative, dermascope, or in process). The bars for lesions for which there are MelaFind results also show icons at the left end. For images that are in process, the bar shows the state of completion in the form of a progressive completion stripe. In cases in which a single scan contained more than one lesion, the lesion status bar is split to show the results for each of the (up to four) lesions in the scan. Each lesion bar is connected by a lead line to the location of the lesion on the model. On the model, the marker for each lesion takes the form of the icon and color corresponding to the icon and color of the lesion status bar. A wide variety of other configurations of bars or other indicators could be used.

The screen of FIG. 42 shows that the views of the model that are shown to the user can be increased or reduced in size, depending on which ones are required to display the locations of the lesions that have been scanned.

In the Hide-Results state, illustrated by the screen of FIG. 43, the lesion status bars show only the state of progress (by a progress bar or the word "completed") of scanning and image processing for images that yield MelaFind results, or simply the word Dermascope, for example.

In some cases, a lesion status bar has an exclamation icon, which indicates that the instruction manual should be consulted for further information.

The lesion thumbnails in the lesion navigation pane all show bars indicating the progress of scanning and image processing.

Figure 44:
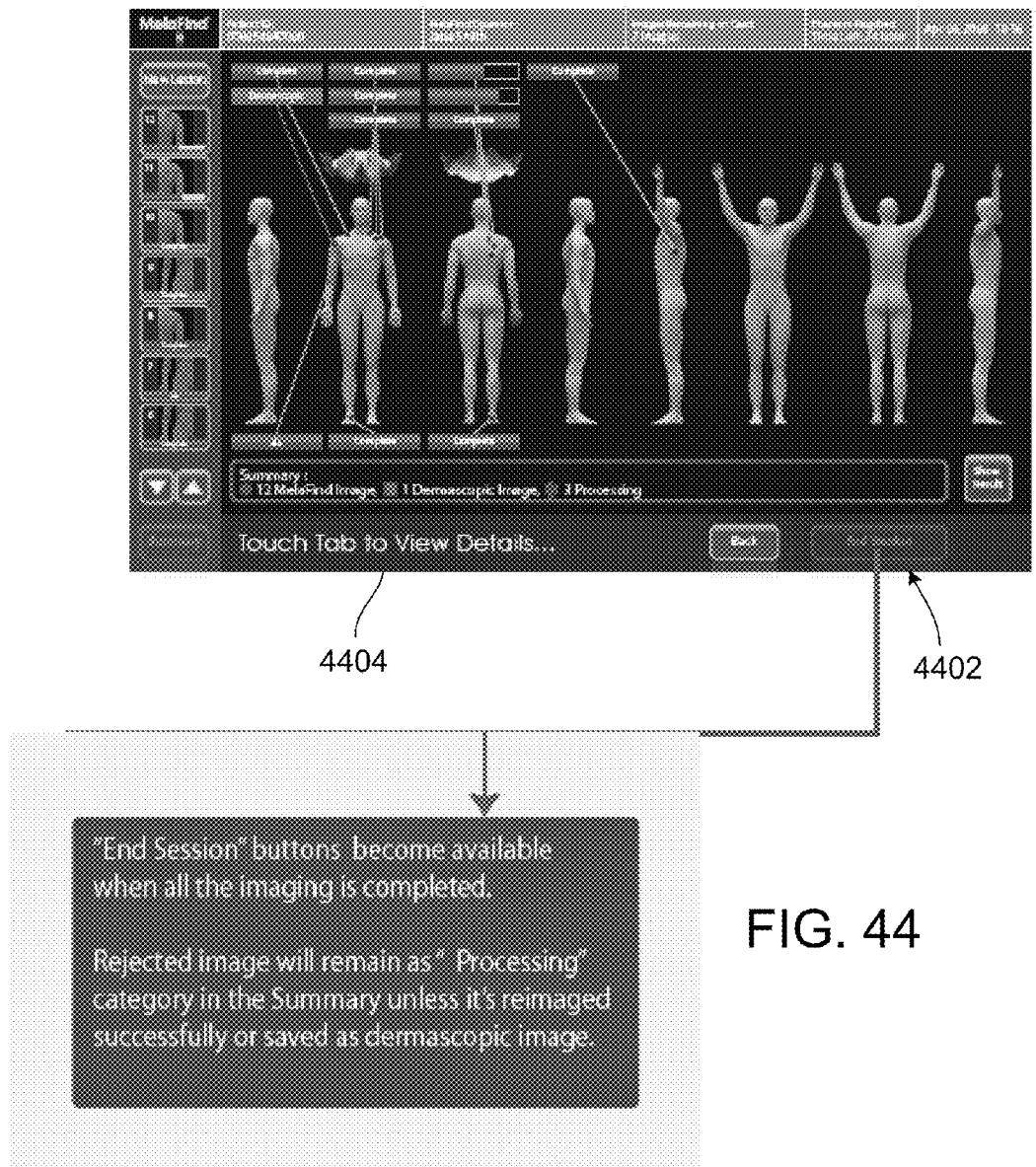

As shown in the screen of FIG. 44 (and in either the Show-Results or Hide-Results state), an End Session button 4402 is displayed. The End Session button becomes active only when all processing of all lesions has been completed. Invoking the End Session button, when it is active, leads to the log-in screen of FIG. 5.

The screens of FIGS. 41 through 44 bear a legend 4404 "Touch Tab to View Details . . . " As an example, if one touches the bar beneath the left-most model image shown in FIG. 41, the detailed display shown in FIG. 35 results.

Figure 45:
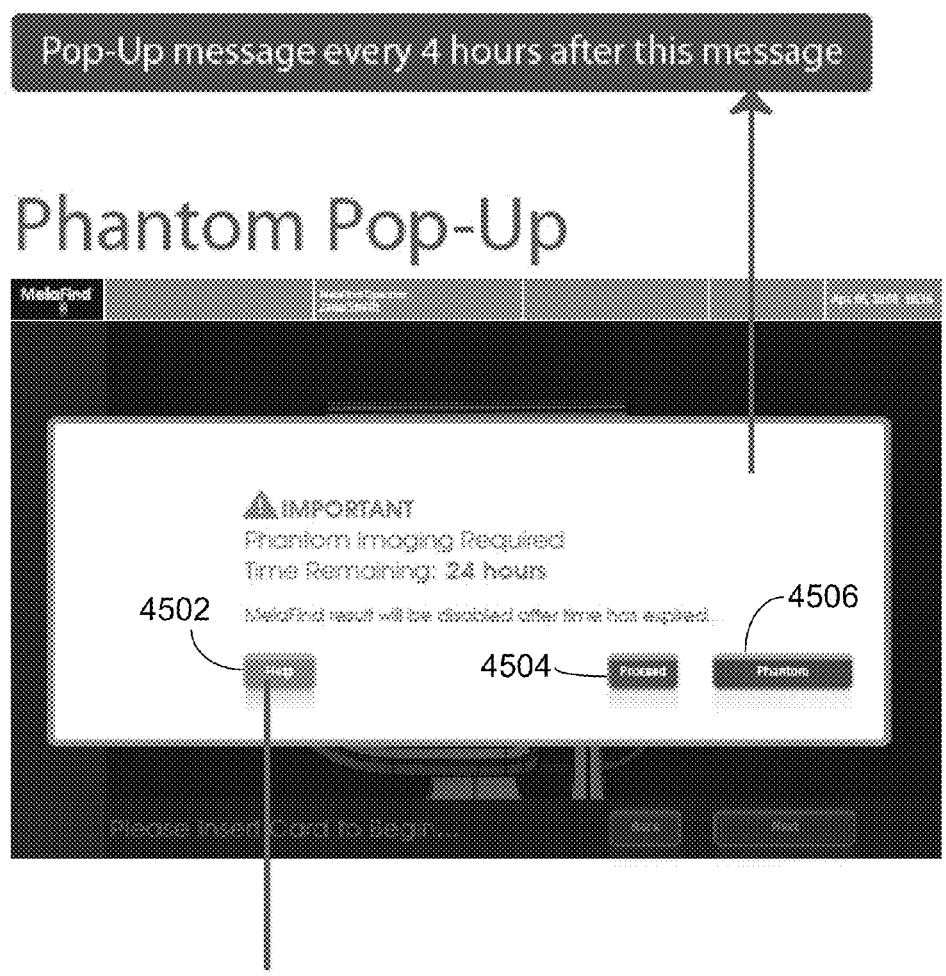
Figure 46:
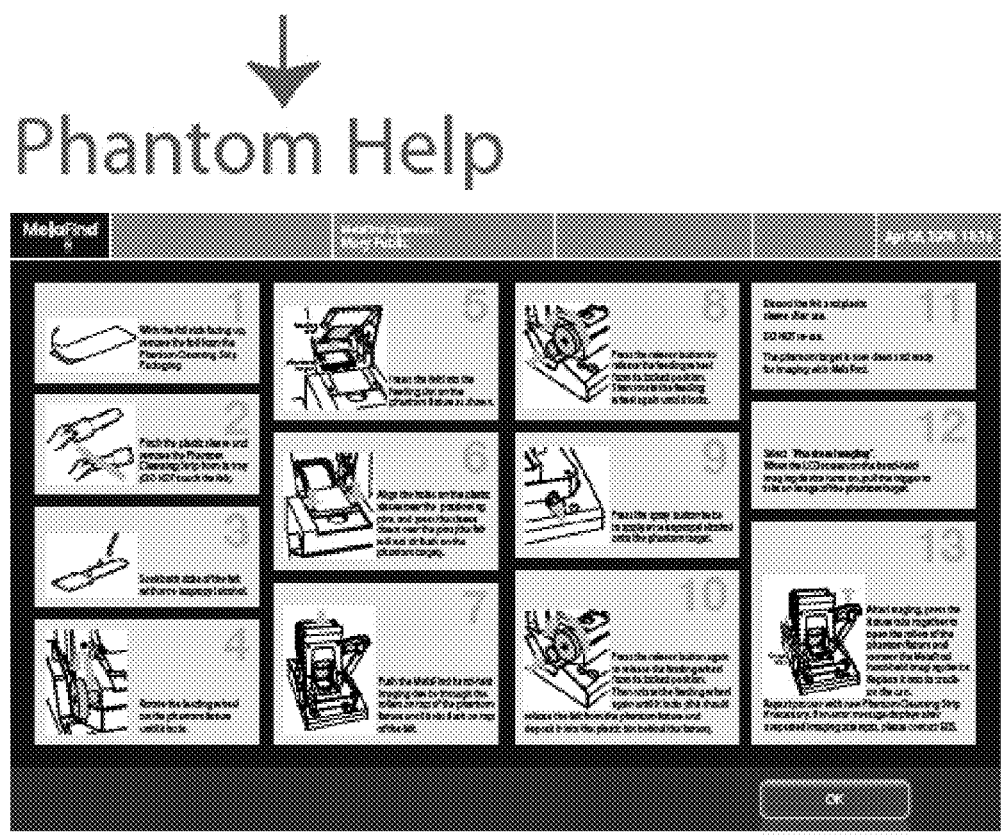
Figure 47:
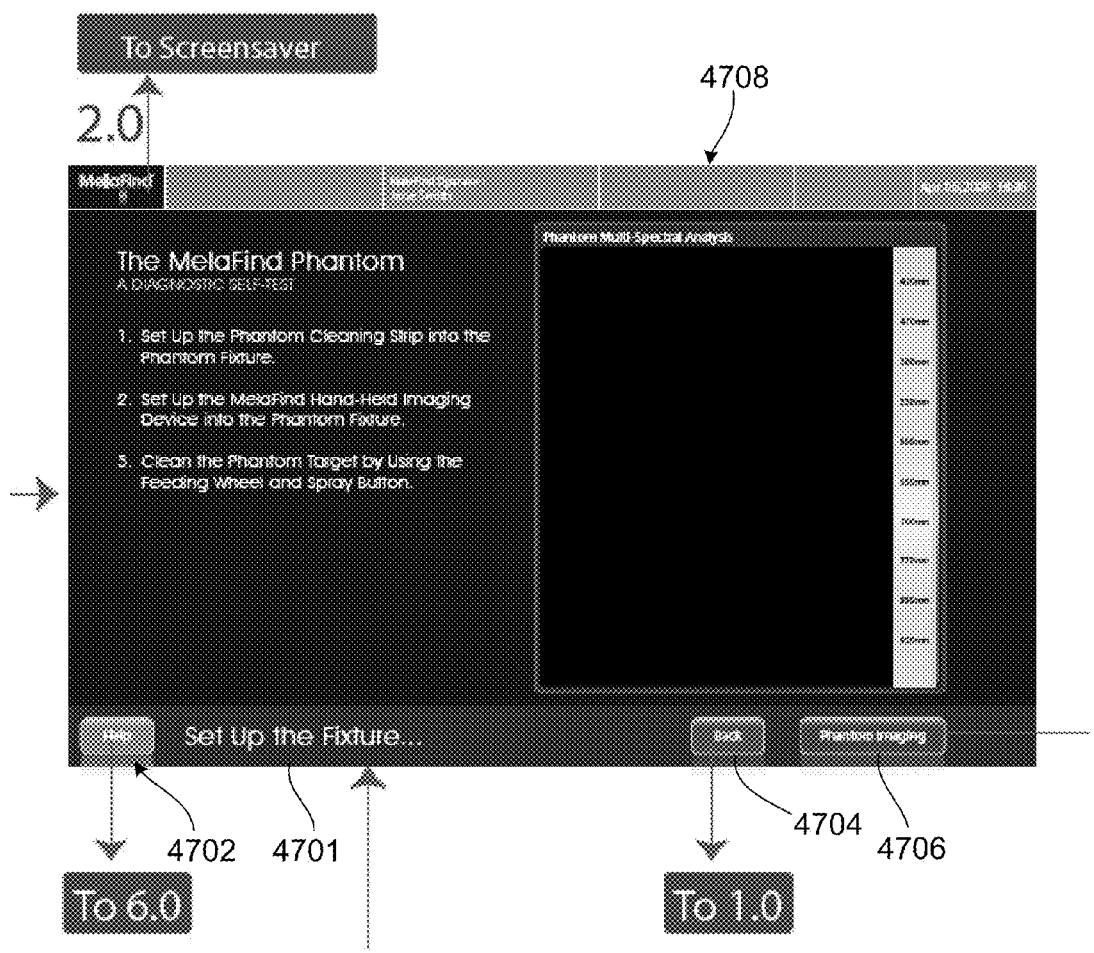
Figure 48:
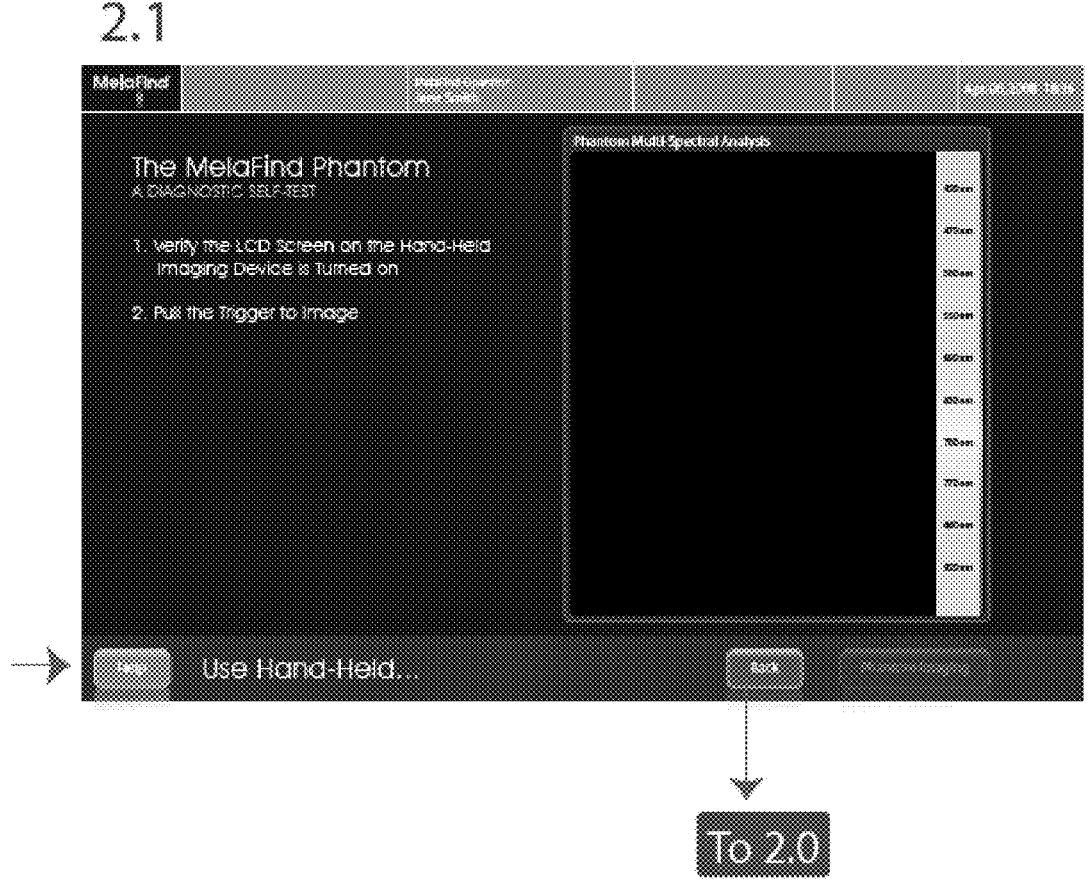

Every four hours, for example, the screen of FIG. 45 is displayed as a pop-up to alert the user how much time remains to "self-test" the probe using the phantom target before the MelaFind Result feature will be disabled. Invoking a Help button 4502 leads to the screen of FIG. 46, which provides instructions for performing the Phantom Imaging self-test. Invoking the Proceed button 4504 extinguishes the pop-up alert for four more hours. Invoking the Phantom button 4506 leads to the Phantom Imaging self-test procedure, the flow of which is shown in FIG. 3.

The screens of FIGS. 47 through 51 provide instructions 4701 to the user to lead the user through successive steps to prepare and scan a phantom target. The Phantom Imaging process can be reached from the appropriate button on the screen of either FIG. 6 or FIG. 45 or FIG. 46.

Figure 49:
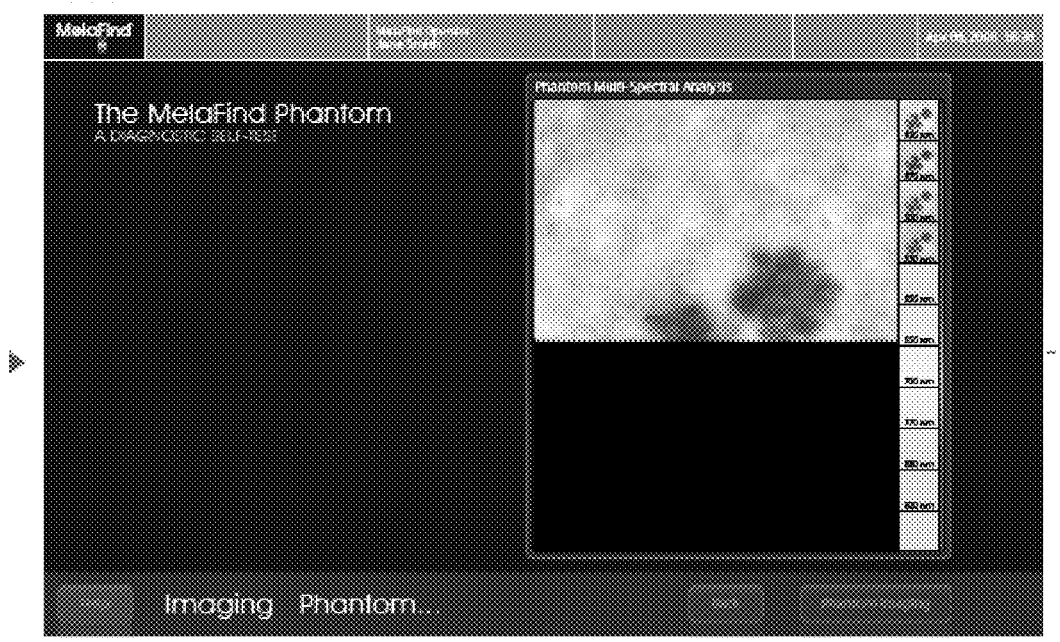
Figure 50:
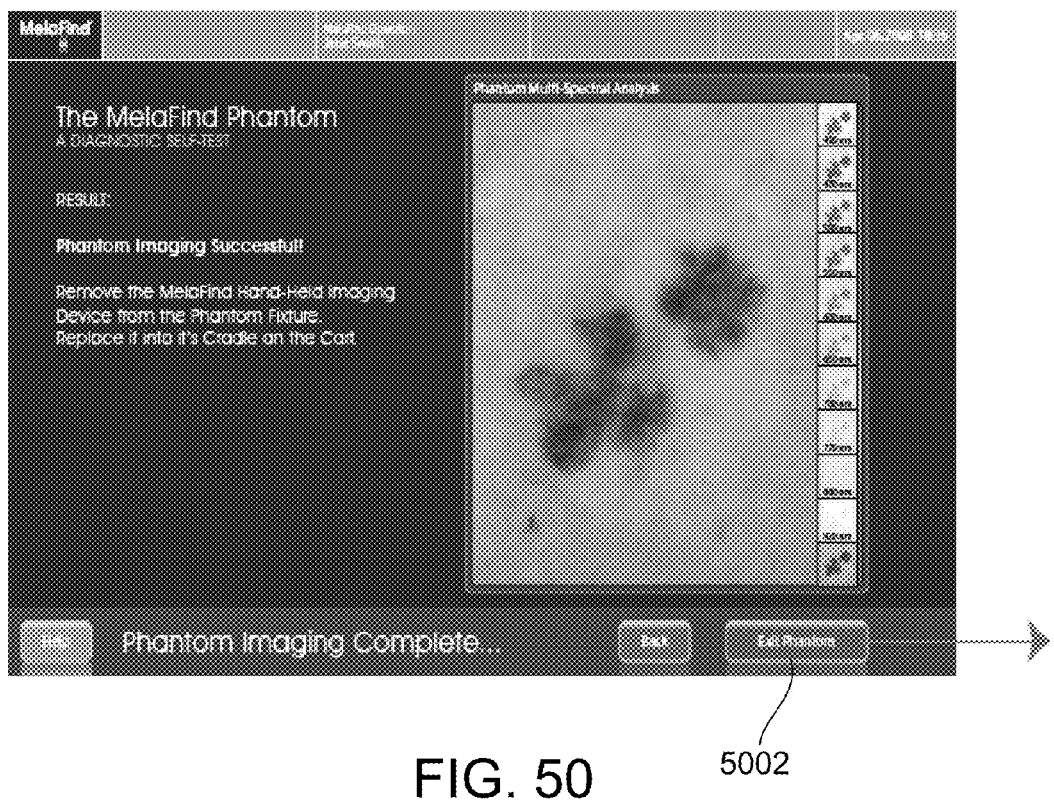
Figure 51:
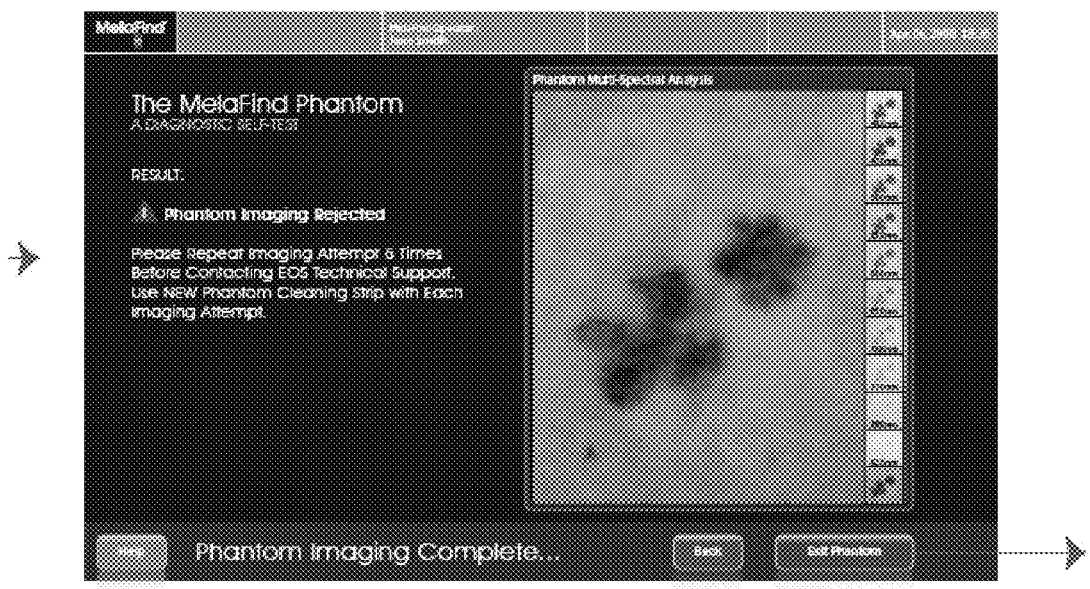
Figure 52:
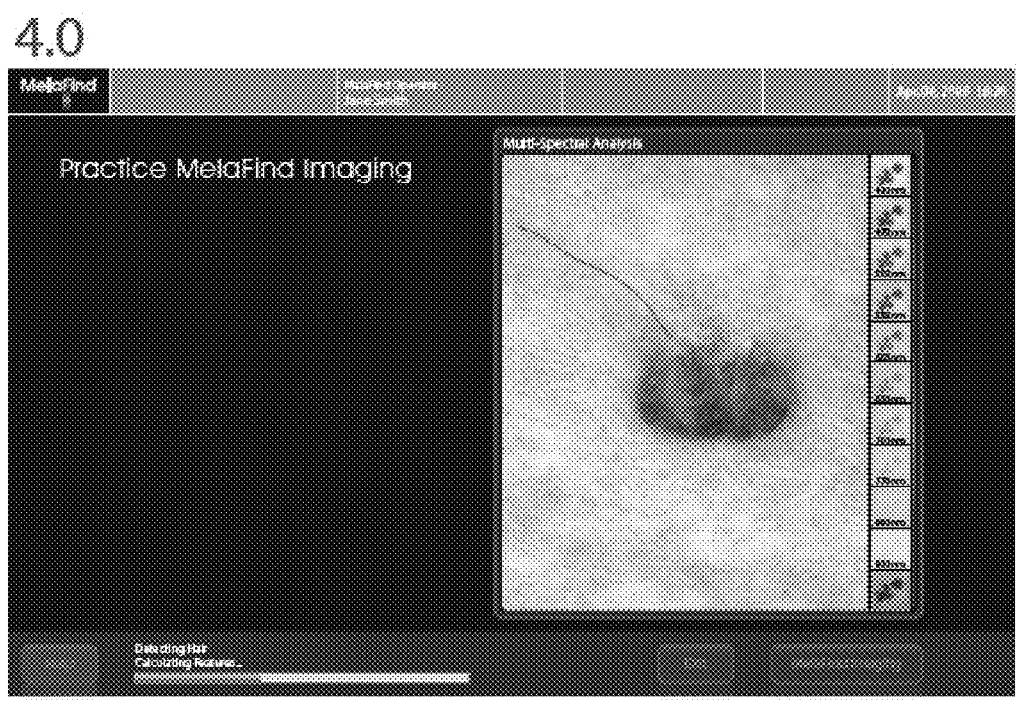

A Help button 4702 always leads to helpful information about that step. A Back button 4704 always returns the user to the prior step. A Phantom Imaging button 4706 arms the system for phantom imaging from the screen of FIG. 47 and leads to the screen of FIG. 48. Pulling the trigger on the hand-held probe then starts the imaging, the progress of which is shown in the screen of FIG. 49, and in its finished state in the screen of FIG. 50, if successful, or of FIG. 51 if not successful. The Exit Phantom button 5002 enables the user to exit the Phantom Imaging procedure.

Figure 53:
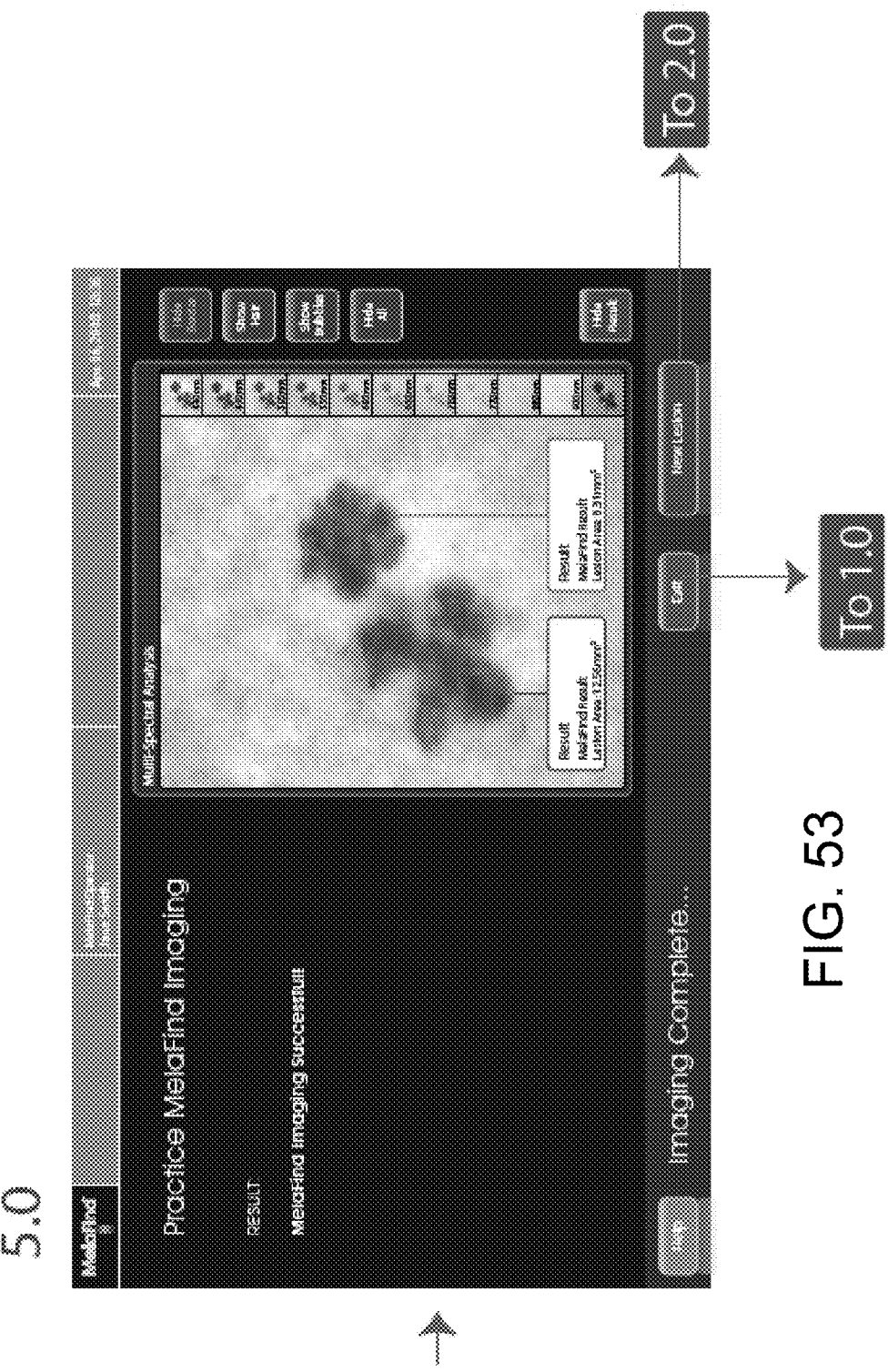
Figure 54:
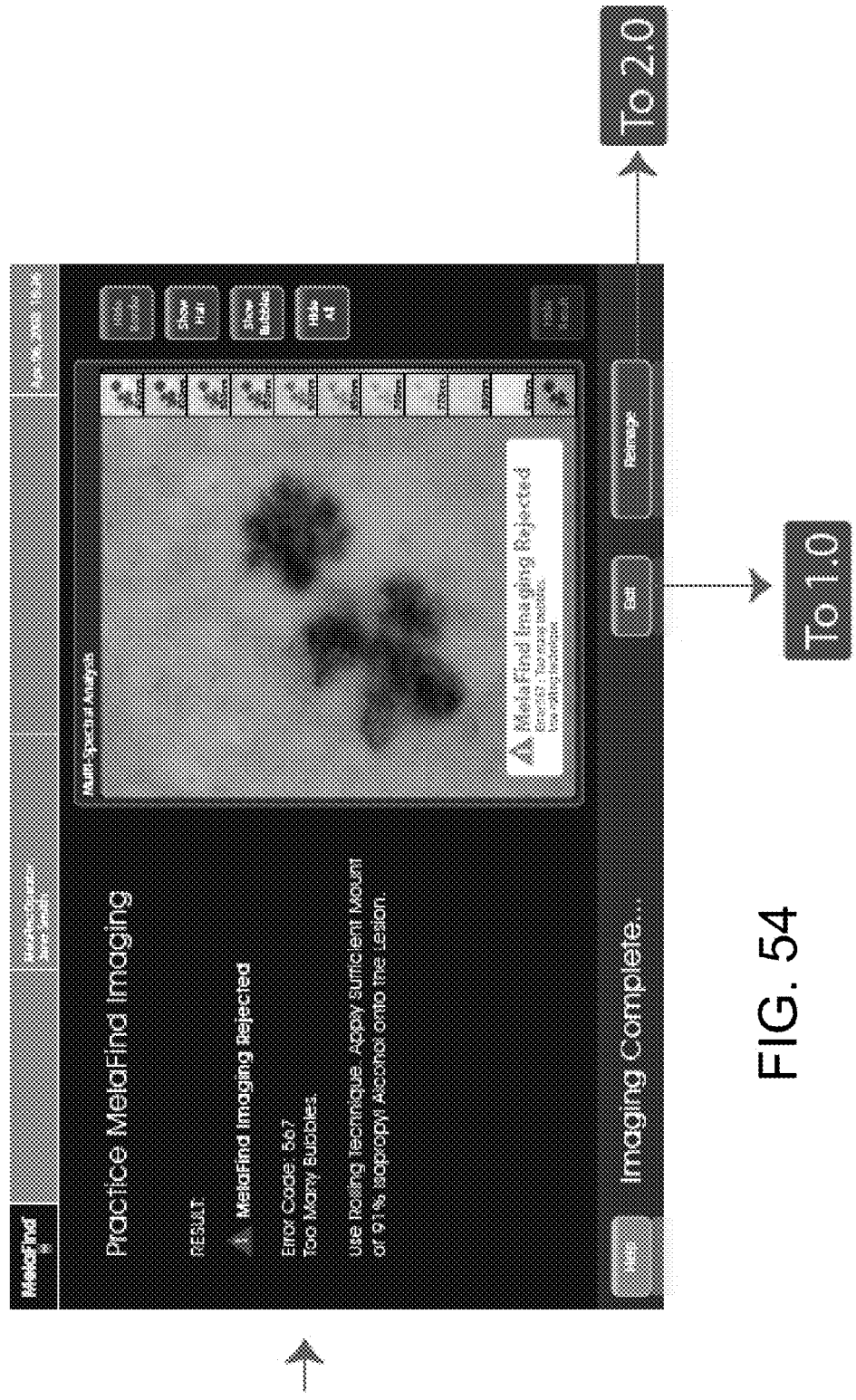
Figure 55:
Figure 56:
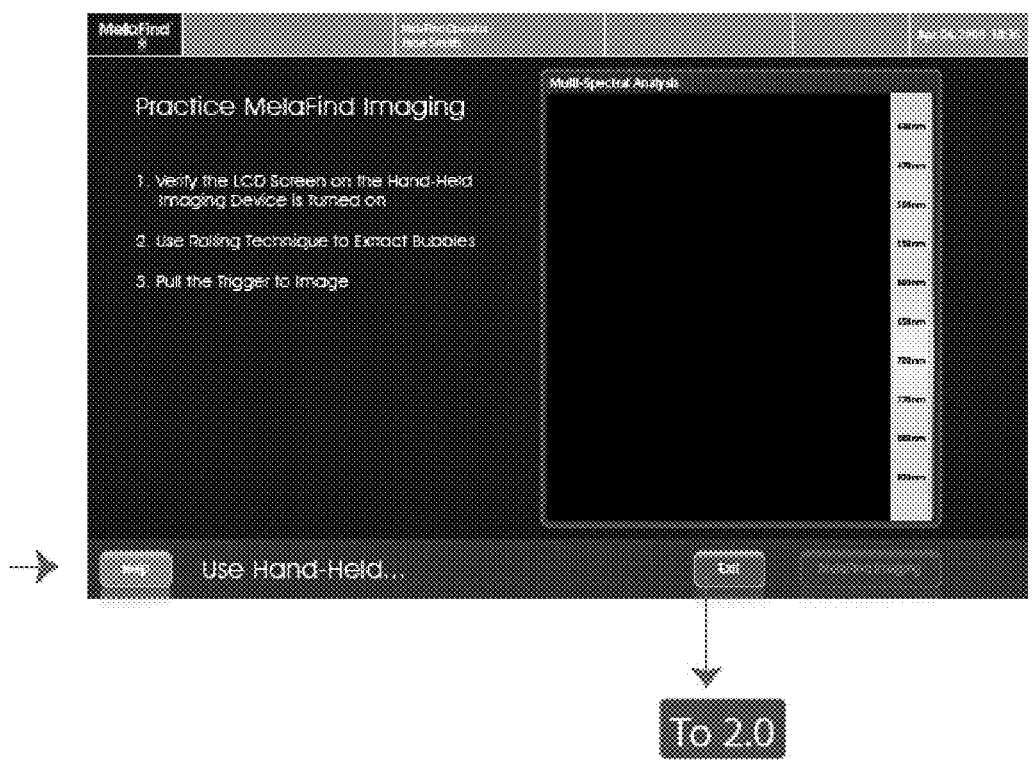

Because the actual use of the memory card to store images of skin lesions on patients has an associated cost, the system provides a Practice mode for scanning, the process of which is tracked in FIG. 4. The sequence is illustrated in the screens of FIGS. 55, 56, 57, 52, and either 53 or 54. As with the Phantom Imaging procedure, the user is provided instructions on successive steps and proceeds from step to step or back, using navigation buttons and the lesion imaging probe, until the scan is either successful (the screen of FIG. 53) or rejected (the scan of FIG. 54), and the user then exits the procedure.

Figure 59:
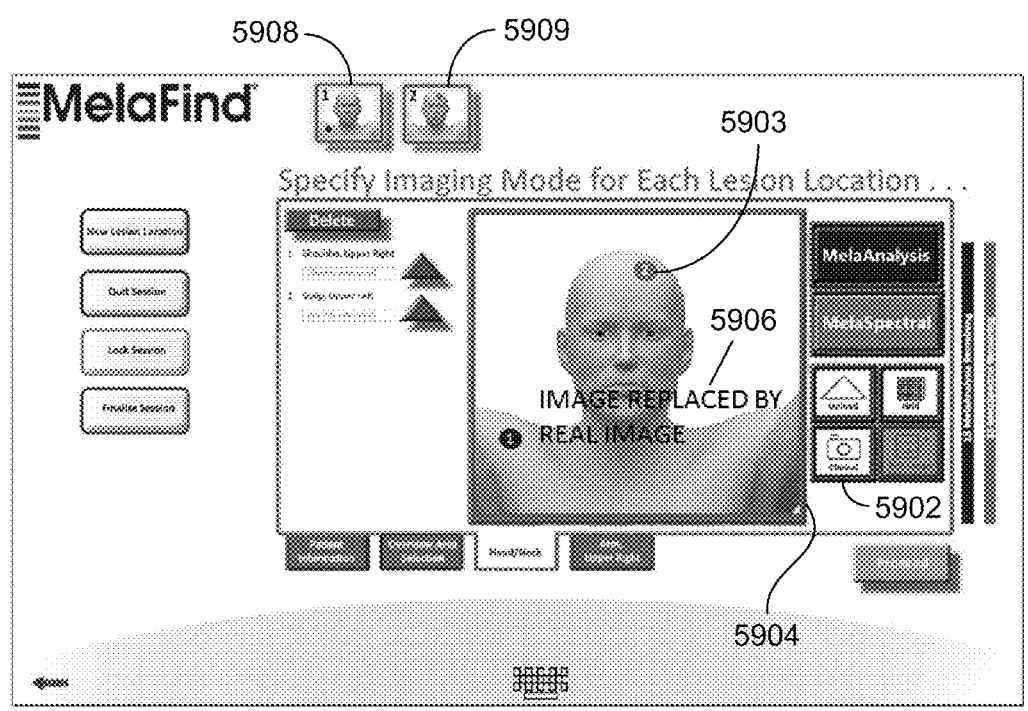

As shown in FIG. 59, during the lesion selection phase, the user can take a picture of the lesion location using a separate digital camera, and can upload the image to the MelaFind® software. In some cases, a reconstructed color image can be selected for the lesion location.

When an image of the lesion is available (either one that is taken using a separate digital camera or one that is reconstructed), that "actual" image can be used to replace, on the model displayed to the user, the close-up model image of the lesion location.

To arrange this substitution of real image for model image of the lesion location, the user invokes the clinical button 5902. Doing so, takes the user to a window that shows available images. When the user selects one of those images, the user is returned to the screen of FIG. 59. The user then clicks on the numbered lesion location 5903 (say, location 2) on the model picture 5904. The system then knows to use the selected real image in place of the model image for that lesion location wherever it is to appear in the user interface (including in other figures shown earlier). A legend 5906 reminds the user that the model image has thus been replaced by the real image. Thumbnails 5908, 5909 can be invoked by the user to view information about any of the lesion locations including the actual images of the lesion locations.

The real image that is substituted for the model image could be a reconstructed dermascopic image, or a traditional dermascopic image, or other kinds of images.

Other features described above with respect to other figures may also apply to the features illustrated in FIG. 59.

Figure 60:
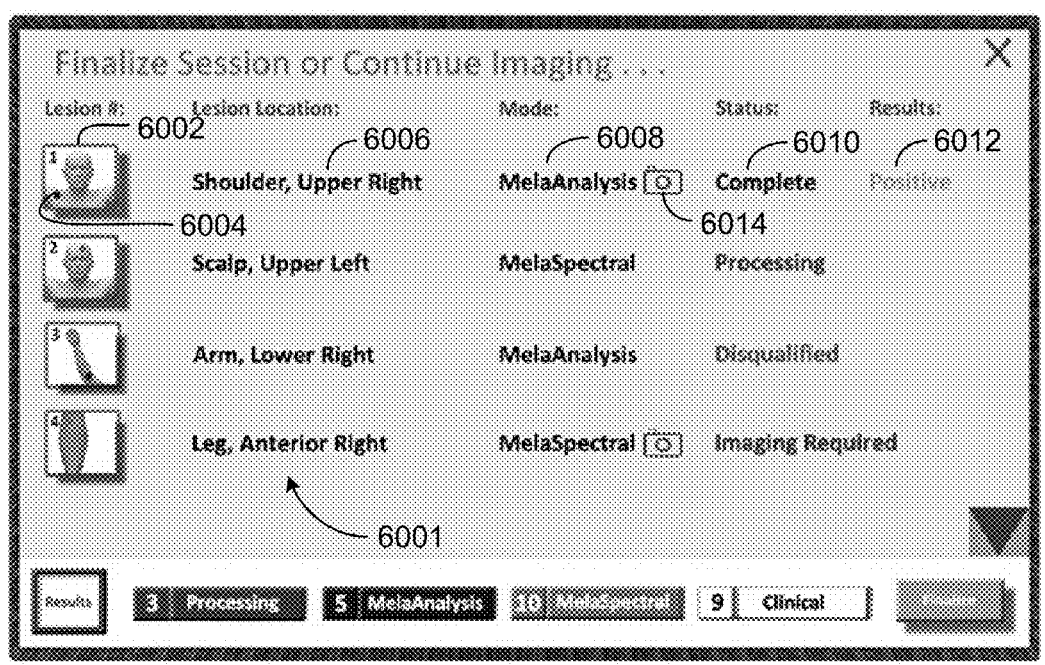

FIG. 60 shows a summary screen of the user interface in which each of the lesion locations is represented in a list 6001 by a thumbnail 6002 in which the location of that lesion is shown by a marker 6004. In each row of the list, the lesion is also identified in terms of location 6006, mode of determination 6008, the status 6010, and the result 6012. When a real image has been substituted for a model image, that fact is represented by a stylized camera 6014. The status indicators can be shown by different colors. The results indicator can be shown by different colors. Other implementations are also within the scope of the following claims.

For example, a wide variety of other types, arrangements, orientations, appearances, and names of the user controls, thumbnails, views, and arrangements of the user interface could be substituted for the examples described above. The sequence of actions and responses of the user interface could also be altered. The coordination and synchronization of different views could be arranged differently. The human models could be made more or less realistic. In some examples, actual photographs of the real human could be substituted for the model photographs. Different sets of human models could be available in selectable by the user to represent real humans of different sizes, shapes, skin coloring, racial features, ages, and other characteristics so that they more directly represent a real human who is the subject of the skin lesion scanning. The kinds of results displayed for each of the lesions could be other than "positive" and "negative" and could be expressed in displayed in other ways. Other navigational devices could be provided to enable the user to move among scans in other ways.

The invention claimed is:
1. A computer-implemented method comprising
showing simultaneously, on a two-dimensional electronic display, (a) at least a partial body view of a surface of a human model on which a location of a skin lesion on a corresponding real human has been indicated, and (b) an image of the lesion area on the real human that corresponds to the location of the skin lesion as indicated on the partial body view of the human model.
2. The method of claim 1 also including showing, simultaneously with the partial body view and the image of the lesion, a thumbnail of the partial body view.

3. The method of claim 1 in which the partial body view bears an indication of the location of the skin lesion.

4. The method of claim 1 in which the image comprises a reconstructed dermoscopic image.

5. The method of claim 1 in which the image comprises a traditional dermoscopic image.

6. The method of claim 1 also comprising enabling a user to choose whether to display the image of the lesion or a model of the lesion.

7. A computer-implemented method comprising:
    showing, on a two-dimensional electronic display, an image that identifies a location of a skin lesion and an indication of the skin lesion on the skin of a real human that corresponds to the shown image of the location of the lesion, and
    showing legends, for the respective skin lesions, each indicating a status of a corresponding skin lesion and a status of a scanned image of the skin lesion.

8. The method of claim 7 in which the image that identifies the location comprises a reconstructed dermoscopic image.

9. The method of claim 7 in which the image that identifies the location comprises a traditional dermoscopic image.

10. The method of claim 7 in which the status of the scanned image comprises progress in completion of an analysis of the image.

11. The method of claim 7 in which the legend comprises a color.

12. The method of claim 7 in which the legend comprises an icon.

13. The method of claim 7 in which the legend comprises a progress bar.

14. A computer-implemented method comprising:
    showing simultaneously, on a two-dimensional electronic display, a list of rows where each row comprises an image representing a lesion location, and a next diagnostic or treatment step in a column-wise list format.

15. The method of claim 14 in which the image comprises a reconstructed dermoscopic image.

16. The method of claim 14 in which the image comprises a traditional dermoscopic image.

17. The method of claim 14 in which the next diagnostic or treatment step comprises biopsy.

18. The method of claim 14 in which the next diagnostic or treatment step comprises observation.

19. The method of claim 14 in which the next diagnostic or treatment step is indicated by a color.

* * * * *